US006917293B2

(12) United States Patent
Beggs

(10) Patent No.: US 6,917,293 B2
(45) Date of Patent: Jul. 12, 2005

(54) INTEGRAL, FLEXIBLE, ELECTRONIC PATIENT SENSING AND MONITORING SYSTEM

(75) Inventor: George R. Beggs, Boulder, CO (US)

(73) Assignee: Tactilitics, Inc., Boulder, CO (US)

( * ) Notice: Subject to any disclaimer, the term of this patent is extended or adjusted under 35 U.S.C. 154(b) by 329 days.

(21) Appl. No.: 10/147,683

(22) Filed: May 17, 2002

(65) Prior Publication Data

US 2003/0216670 A1 Nov. 20, 2003

(51) Int. Cl.$^7$ ............................................... G08B 23/00
(52) U.S. Cl. ..................... 340/573.1; 340/666; 340/667
(58) Field of Search ........................... 340/573.1, 573.4, 340/666, 667; 600/595

(56) References Cited

U.S. PATENT DOCUMENTS

| | | | |
|---|---|---|---|
| 4,020,482 A | | 4/1977 | Feldl |
| 4,179,692 A | | 12/1979 | Vance |
| 4,228,426 A | | 10/1980 | Roberts |
| 4,295,133 A | | 10/1981 | Vance |
| 4,539,560 A | | 9/1985 | Fleck et al. |
| 4,633,237 A | | 12/1986 | Tucknott et al. |
| 4,684,767 A | | 8/1987 | Phalen |
| 4,845,323 A | | 7/1989 | Beggs |
| 5,113,176 A | * | 5/1992 | Harris ...................... 340/573.7 |
| 5,140,309 A | | 8/1992 | Gusakov |
| 5,144,284 A | | 9/1992 | Hammett |
| 5,325,551 A | * | 7/1994 | Tappel et al. ................... 5/709 |
| 5,473,313 A | * | 12/1995 | Graebe, Jr. ................. 340/667 |
| 5,654,694 A | * | 8/1997 | Newham .................. 340/573.1 |
| 5,844,488 A | * | 12/1998 | Musick .................... 340/573.4 |
| 6,030,351 A | * | 2/2000 | Schmidt et al. ............. 600/595 |
| 6,255,956 B1 | * | 7/2001 | Tingley et al. .............. 340/667 |
| 6,289,238 B1 | | 9/2001 | Besson et al. |
| 6,297,738 B1 | | 10/2001 | Newham |
| 6,549,140 B1 | * | 4/2003 | Koessler .................. 340/573.1 |
| 6,646,556 B1 | * | 11/2003 | Smith et al. ............. 340/573.1 |

FOREIGN PATENT DOCUMENTS

| | | |
|---|---|---|
| WO | WO 01/64103 | 9/2001 |
| WO | WO 01/95848 | 12/2001 |
| WO | WO 03/017221 | 2/2003 |

* cited by examiner

Primary Examiner—Thomas Mullen
(74) Attorney, Agent, or Firm—Faegre & Benson LLP

(57) ABSTRACT

A self contained patient sensing and monitoring system is provided for sensing and monitoring the presence, absence, and movement of the patient. Embodiments of the present invention provide a system conformable to a patient support surface, systems that are self contained, systems that are operationally unobtrusive, and programmable systems. Embodiments of the present invention comprise a container, a sensor configured within the container, and a control unit responsive to the sensor and configured within the container, wherein the container at least substantially encompassing the sensor and the control unit and wherein the control unit is conformable to the patient support surface. Some embodiments of the present invention comprise a container, a sensor configured within the container, and a control unit conformable to a patient support surface and configured within the container, wherein said control unit is responsive to the sensor. Embodiments of the present invention may also comprise a sensor, a signal conditioner responsive to the sensor, a processor configured to comprise instruction and data and to which the signal conditioner is configured to provide signals generated by the sensor, at least one storage media, wherein the instructions and data are stored on the at least one storage media, and at least one input connection capable of providing programmable input to the storage media and the processor. Methods are also disclosed for sensing and monitoring the presence, absence, and movement of a patient. The inventive concept can be used in various applications, such as a bed, mattress, chair, or wheelchair, to achieve the monitoring of the presence, absence, and movement of a patient.

86 Claims, 14 Drawing Sheets

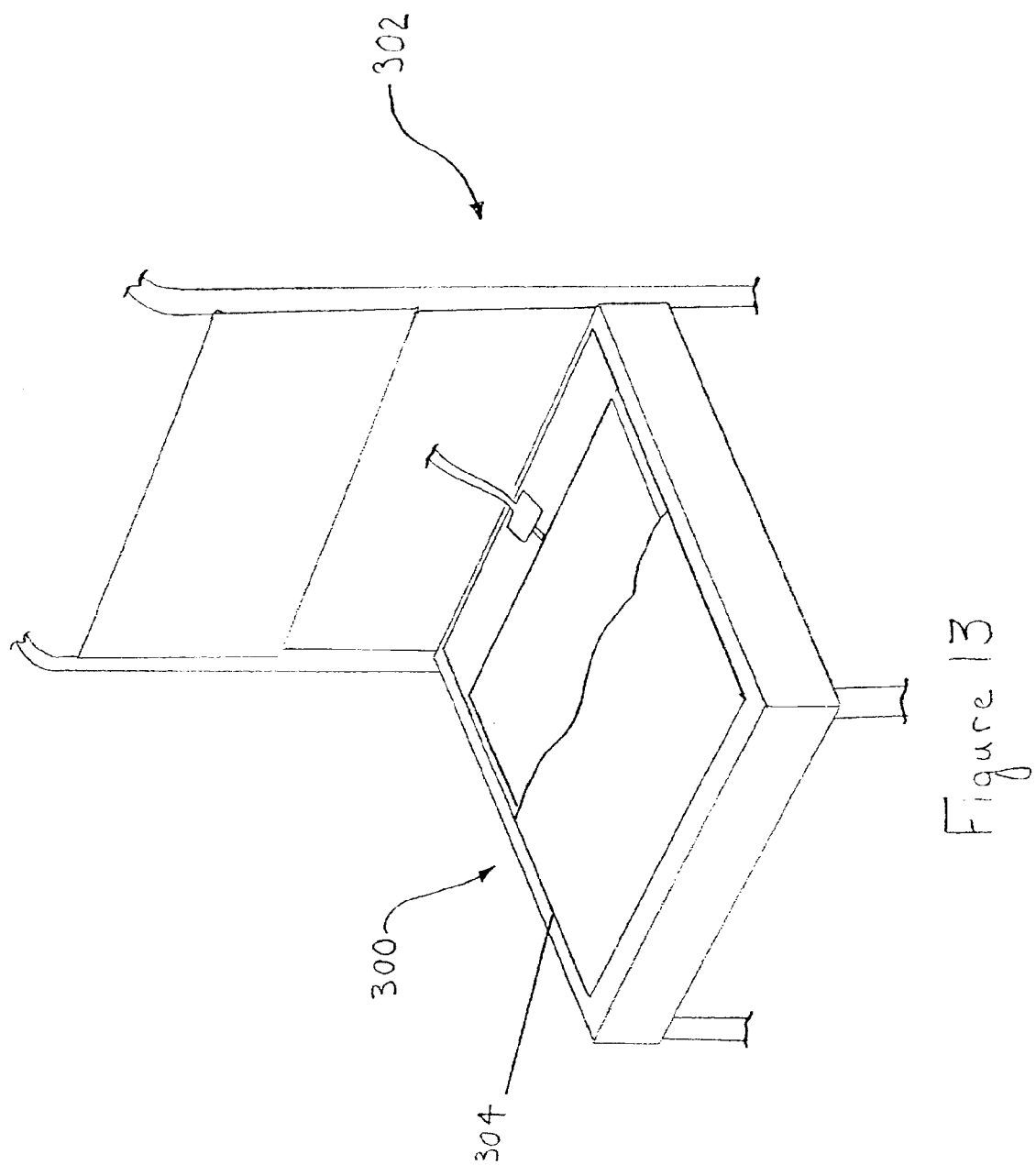

INTEGRAL, FLEXIBLE, ELECTRONIC PATIENT SENSING AND MONITORING SYSTEM

BACKGROUND OF THE INVENTION

1. Field of the Invention

The present invention relates generally to health fields involving patient care. Specifically, the present invention relates to sensing and monitoring systems providing for sensing and monitoring of patient movement and further relates to systems providing for the determination of the presence or absence of a patient. Embodiments of the present invention provide systems that may be implemented in a bed, chair, wheelchair, or other configurations. The present invention provides a patient sensing and monitoring system which allows for system control, sensing, and monitoring in a configuration that is self-contained. The invention may be especially applicable for patient sensing and monitoring as a system which provides programmable control and the ability for health care personnel to monitor patients remotely.

2. Description of the Related Art

Monitoring the presence of patients in a bed, chair, wheelchair, or the like, is a significant problem for many care facilities, such as hospitals and nursing homes. Patients are typically expected to remain in their bed to protect them from injuring themselves if they should exit from bed unassisted and become injured due to their weakened physical condition or other physical or mental impairment. It is important, therefore, for care providers to be notified quickly when a patient leaves a bed. This problem is serious in all health care settings, including hospitals, assisted living, and home care and is especially pronounced in nursing homes, where a large percentage of these facilities' patients are in weakened physical conditions. Physical restraints on patients, which were used routinely in the past to address these problems are now rarely practical or acceptable.

Therefore, care facilities have begun to address this growing problem by utilizing a variety of devices that monitor patient movement. For example, U.S. Pat. No. 4,854,323 to Beggs, No. 4,633,237 to Tucknott et al., No. 4,179,692 to Vance, No. 5,144,284 to Hammett, and No. 4,228,426 to Roberts describe a number and variety of sensing devices developed to address some of the needs of the care facilities in monitoring presence or absences of patients on beds.

A conventional bed monitoring device 2 is shown in FIG. 1. Generally, such a monitoring device 2 has a flexible, elongated, pressure-sensitive, switch 6 to sense by closed or opened electric switch contact the presence or absence of a patient P from a bed B. When the patient P is present on the bed B, as illustrated in FIG. 1, the elongated, flexible, switch 6 has closed electric contacts (not shown in FIG. 1). However, if the patient P leaves the bed B or, in some cases, when the patient P merely moves, the electric contacts of switch 6 open. Such closed switch or opened switch conditions create an opened or closed electric circuit on cord 4, which is sensed by a controller an interface box 8 connected to the cord 4. The controller in interface box 8, in response, produces a signal that is in the same format, i.e., mimics, a signal from a conventional nurse call button N. therefore, such a signal from the interface box 8, when connected by another cord 9 to a conventional nurse call circuit C via a conventional nurse call wall connector or socket in the patient's room, activates a light and/or audible alarm of a conventional nurse station monitor M at a remote location to notify the nurse to check on the well-being of the patient P.

In other words, the signal produced by the bed monitoring device 2 is indistinguishable from the signal produced by the conventional nurse call button N, and the nurse call station monitor responds the same to both of them. If the switch portion 6 of the bed monitoring device 2 was connected directly to the nurse call circuit C without the interface box 8, similar to a nurse call button N, it would activate the nurse call monitor M every time the patient P gets out of bed B, even momentarily, and even whenever the patient P moves on the bed B in a manner that removes his or her weight from the switch portion 6. The conventional nurse call monitor M simply responds to a signal on the nurse call circuit C and has no way of distinguishing acceptable patient P activity from patient absence from the bed B that needs attention. Consequently, state-of the-art bed monitors 2 need the controller of interface box 8 to intercept signals from the switch portion 6 and to process such signals in a manner necessary to produce only suitable nurse call signals for the nurse call circuit C. Therefore, the controller in interface box 8 may have logic that produces output signal on cord 9 only after switch portion 6 remains open for some preset time threshold, such as 3–6 seconds, and it may have other features, such as on/off and reset switches, audio and/or visual alarm, timer adjustment, information recorder, and the like.

While the switch portion 6 of the conventional bed monitoring device 2 is flexible, conformable to a soft and deformable bed B surface, and non-obtrusive so as to be comfortable and virtually not noticeable to the tactile senses of the patient P, the conventional interface box 8 is a problem. It is hard, bulky, requires an extra cord 9, and is generally obtrusive and adds to the clutter in typical small and restricted spaces of patient rooms in hospitals and nursing care facilities.

Therefore, some areas in care facilities may lack sufficient space to accommodate the interface box 8 and multiple cords 4, 9 of conventional bed monitor equipment 2, especially if other patient care equipment is necessary, such as equipment monitoring the vital signs of the patient, tray tables, intravenous feeding tubes and stands, nurse call cords and buttons, catheter tubes and bags, leg stimulator drivers and tubes, traction bars and cords, patients' personal effects, and the like. Components of conventional bed monitoring equipment 2, such as the interface box 8, are also inadequately configured to be placed in operationally unobtrusive locations in relation to the working area necessary for nurses, doctors, and other care-giving staff to have accessibility to the patients. For example, placement of components of conventional bed monitoring equipment 2, interface box 8 and cords 4, 9, a patient support surface of a bed B, mattress, or seat of a chair or wheelchair, would detract from the comfort of the patient P, make control of the equipment less accessible, and could compromise the functionality of the system. Further, conventional monitoring systems such as those previously described, which have hardwire or cable connection to external equipment, such as the nurse call circuit C or other monitoring equipment, actually teach away from operationally unobtrusive system features. Consequently, conventional bed monitoring equipment 2 has excessive, obtrusive wire connections and bulky components and tend to restrict busy health care professionals ability to perform their patient care functions and duties.

Consequently, there remain strong and unmet needs for a reliable, simply configured, less complex, and less costly system that can provide care facilities with the necessary control functions and the abilities to remotely monitor the movement, presence, or absence of patients who are confined to beds, chairs, wheelchairs, or other equipment or locations.

SUMMARY OF THE INVENTION

Accordingly, it is a general object of the present invention to provide a reliable, simply configured, operationally less complex, and less obtrusive system for remotely monitoring the presence, absence, or motion of a patient in a bed, wheelchair, or similar device.

Another general object of the invention is to provide a bed monitoring system that contributes less to clutter in and around a patient's bed in a hospital or nursing care facility.

A more specific object of this invention is to eliminate the need for the bulky, obtrusive, interface boxes of conventional patient bed monitoring equipment, while maintaining desired functionalities, including, but not limited to, providing reliable signals for a nurse call system in an appropriate format for actuating a nurse call monitor with a minimum of false alarm and other problems.

It is a related object of the present invention to provide a system for monitoring a patient's presence, absence, or motion that provides improved reliability, especially over erroneous signals such as false alarms.

It is a further related object of the present invention to provide a system for monitoring a patient's presence, absence, or motion that can be readily integrated into existing care environments and that accommodates for physical limitations of patient care facilities, especially space considerations and multiplicity of wires and connections.

It is also a related object of the present invention to provide a system for monitoring a patient's presence, absence, or motion that provides an adequately controllable configuration, especially control that is less user-obtrusive.

Further, it is also a related object of the present invention to provide a system for remotely monitoring a patient's presence, absence, or motion that is operationally unobtrusive and that allows for advanced system features such as transmission of generated signals to a wireless receiver, potentially a receiver worn by a health care professional.

It is a further, related object of the present invention to provide a self-contained system for sensing and monitoring a patient's presence, absence, or motion and that further provides desirable compact and low-profile configurations and that is conformable in shape and contact with regard to a supporting surface in applied applications, such as a bed, mattress, chair, or wheelchair.

Additional objects, advantages, and novel features of the invention are set forth in part in the description that follows and others will become apparent to those skilled in the art upon examination of the following description and figures or may be learned by practicing the invention. Further, the objects and the advantages of the invention may be realized and attained by the instrumentalities and in combinations particularly pointed out in the appended claims.

To achieve the foregoing and other objects in accordance with the purposes of the present invention, as embodied and broadly described herein, a self contained, operationally unobtrusive patient sensing and monitoring system conformable to a patient support surface is disclosed. The system comprises a container, a sensor configured within the container, and a control unit responsive to the sensor and configured within the container, wherein the container at least substantially encompasses the sensor and the control unit and wherein the control unit is conformable to the patient support surface.

Embodiments of a self contained, operationally unobtrusive patient sensing and monitoring system are also disclosed comprising a container, a sensor configured within the container, and a control unit conformable to a patient support surface and configured within the container, wherein the control unit is responsive to said sensor. Further, a self contained, operationally unobtrusive patient sensing and monitoring system according to the present invention comprises a sensor, a signal conditioner responsive to the sensor, a processor configured to comprise instruction and data and to which the signal conditioner is configured to provide signals generated by the sensor, at least one storage media, wherein the instructions and data are stored on the at least one storage media, and at least one input connection capable of providing programmable input to the storage media and the processor.

To further achieve the foregoing and other objects in accordance with the purposes of the present invention, as embodied and broadly described herein, a method of operationally unobtrusively sensing and monitoring a patient is disclosed. The method comprises providing a sensor at least substantially encompassed by a container; providing a control unit responsive to the sensor and at least substantially encompassed by the container; conformably positioning the encompassed sensor and control unit to a patient support surface of an application; monitoring for the presence, absence, or movement of a patient; detecting an open circuit configuration of the sensor and control unit corresponding to the absence of patient contact with the sensor; measuring an amount of time corresponding to the open circuit configuration and the absence of patient contact with the sensor, determining if the amount of time exceeds a threshold delay period; transmitting an alarm signal corresponding to the absence of the patient upon the step of determining if said amount of time exceeds a threshold delay period; detecting a closed circuit configuration of the sensor and control unit corresponding to the presence of the patient contact with the sensor; and transmitting patient movement information responsive to the step of detecting a closed circuit configuration.

Embodiments of a method of operationally unobtrusively sensing and monitoring a patient are also disclosed, comprising providing a sensor configured within a container; providing a control unit responsive to the sensor and configured within the container; conformably positioning the sensor and control unit to a patient support surface of an application; conforming the sensor and control unit to a patient support surface of said application; monitoring for the presence, absence, or movement of a patient; transmitting an alarm signal corresponding to the absence of the patient contact with the sensor.

A method for detecting a signal representing the presence, absence, or movement of a patient according to the present invention comprises providing a sensor conformable to a patient support surface; programming a control unit conformable to a patient support surface and configured to comprise instruction and data stored on at least one storage media; positioning a patient on the sensor; generating at least one signal from the sensor corresponding to the presence, absence or movement of a patient; conditioning said at least one signal; processing the at least one signal with the control unit; determining patient movement information by the control unit; transmitting patient movement information; transmitting at least one alarm signal corresponding to the presence, absence or movement of the patient; and receiving patient movement information and the at least one alarm signal at external patient monitoring equipment.

BRIEF DESCRIPTION OF THE DRAWINGS

The accompanying drawings, which are incorporated in and form a part of the specification, illustrate the preferred embodiments of the present invention, and together with the written description and claims, serve to explain the principles of the invention. In the drawings:

FIG. 13 is a perspective view of an alternate embodiment of the patient sensing and monitoring system of this invention in a chair or wheelchair configuration;

DETAILED DESCRIPTION OF PREFERRED EMBODIMENTS

The basic concepts of the invention may be embodied in many different ways. As should be understood, the present invention includes a variety of aspects that may be used in various combinations. The invention encompasses a variety of embodiments of patient sensing and monitoring systems, apparatus, device, processes, and methods. The invention involves both methods and devices or apparatus to accomplish the various aspects explained. In addition, while example systems and methods of the present invention are disclosed, including preferred embodiments, to facilitate explanation of the invention, it should be understood that these embodiments may be varied in accordance with the entire disclosure of the present invention. Importantly, as to all of the foregoing, all aspects should be understood to be encompassed by this disclosure both independently and in combination as set forth in the claims now or later issued, in both this and in subsequent continuing applications, if any.

Figure 1:
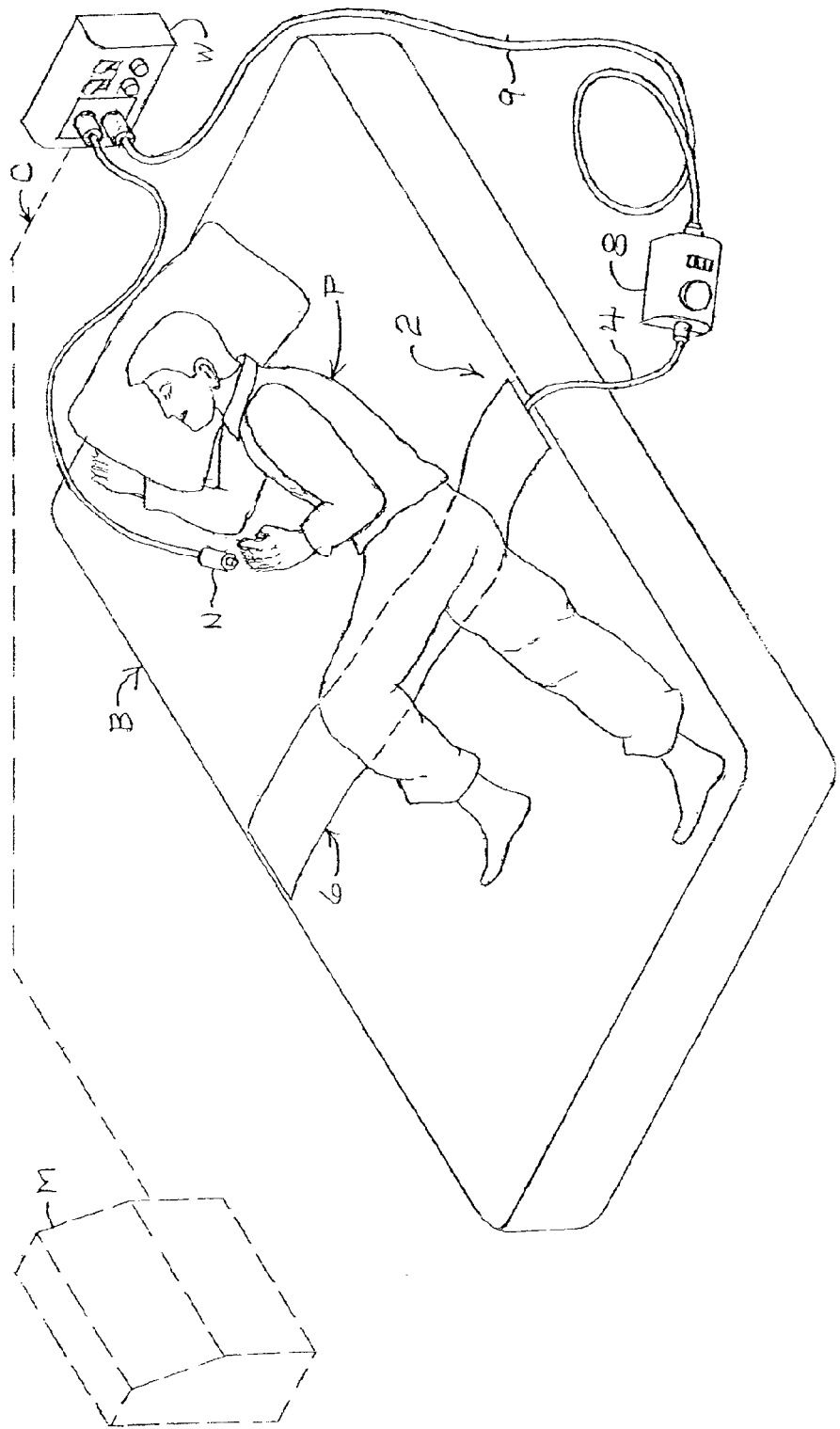
FIG. 1 is an isometric view of a conventional, prior art, bed exit monitoring device for a patient bed with an external controller interface box.
Figure 2:
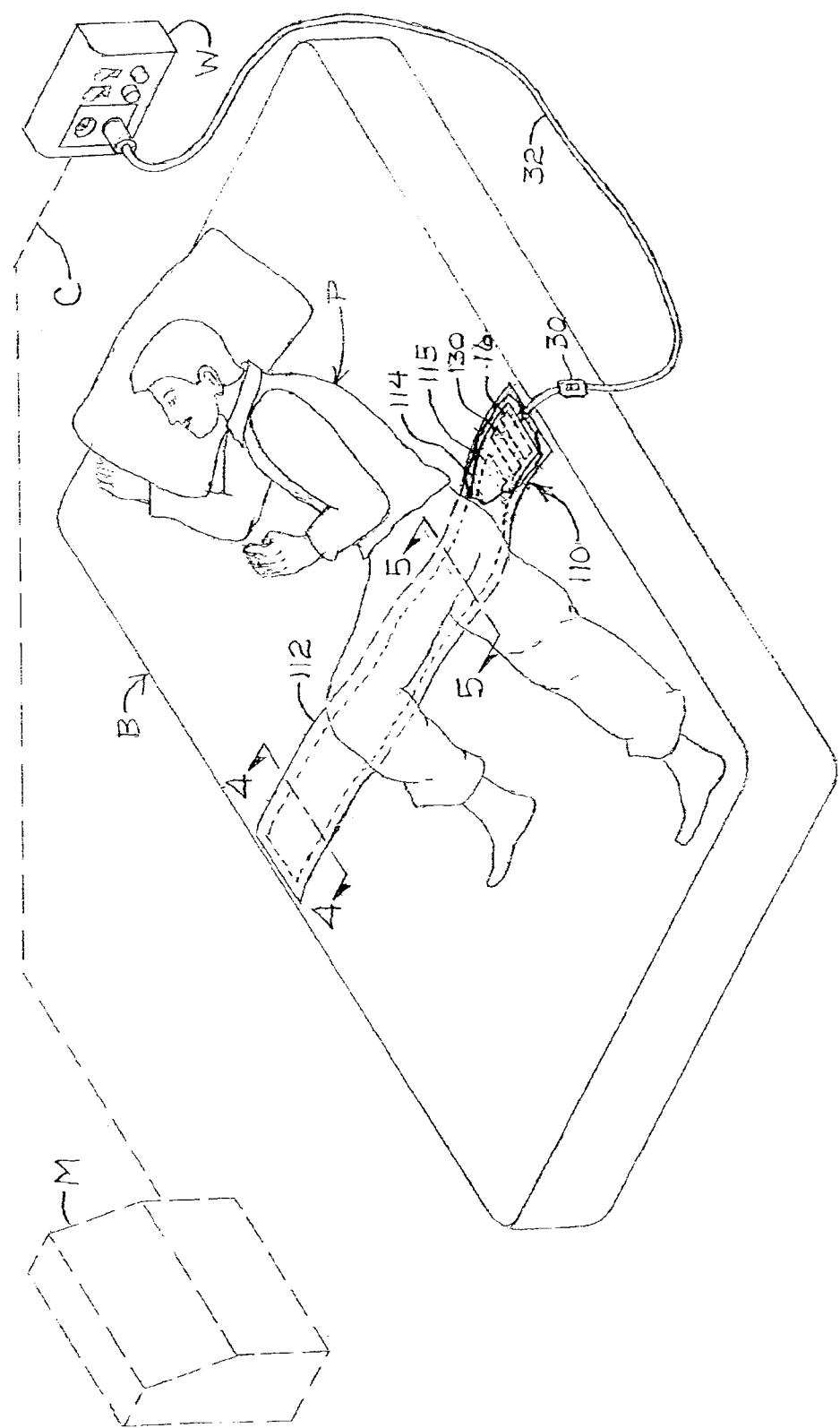
FIG. 2 is an isometric view of one embodiment of the patient bed monitoring apparatus of the present invention with a portion of the cover or sheath cut away to reveal internal controller and flexible battery strip components of the apparatus.
Figure 3:
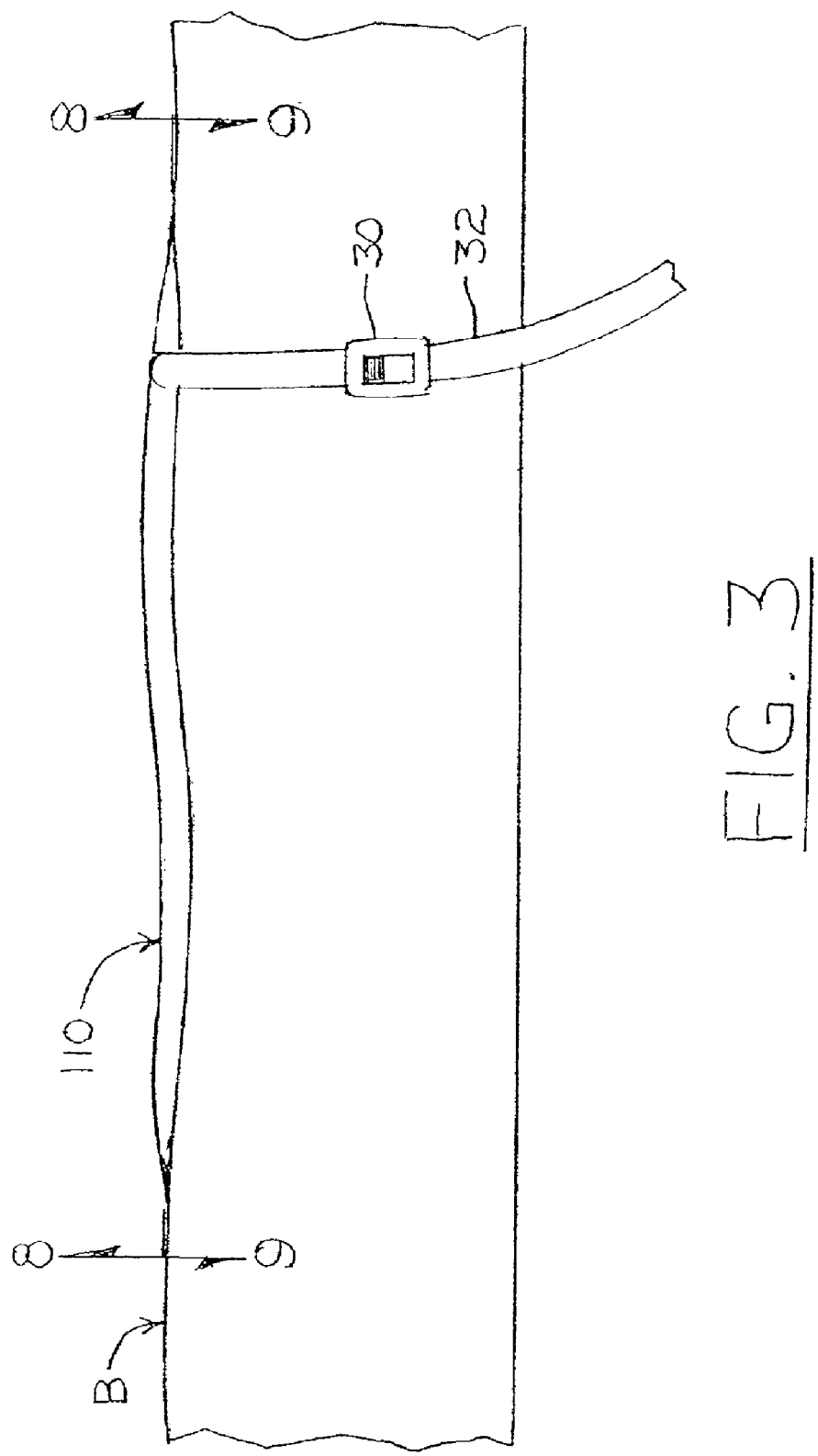
FIG. 3 is an enlarged, end elevation view of the patient bed monitoring apparatus in FIG. 2.

One embodiment of a patient sensing and monitoring system 10 according to this invention is, shown in FIG. 2. This system 110 is capable of sensing and monitoring at least some movement, but is primarily for detecting presence, or absence of a patient P on a bed B, although other embodiments can be sized and configured for use on other mattresses, chairs, wheelchairs, or other support surfaces, as will be explained in further detail below. This embodiment of the patient sensing and monitoring system 110 is configured for use in a conventional hospital bed B for activating a conventional nurse call system monitor M.

The system 110 includes an integral, flexible, electronic sensing and control device 114, which is adapted to be placed on a patient's bed B under the patient P, so that the patient's weight applied on the device 114 causes a first condition in the device 114 indicative of the patient's presence on the bed B. In contrast, the absence of the patient's weight on the device 114 causes a second condition in the device 114, which is indicative at least that the patient P has moved on the bed B and may be indicative of the possibility that the patient P may have left the bed B. The integral sensing and control device 114 is preferably long enough to extend transversely across the bed B and is preferably flexible along its entire length so that it can conform to a soft and deformable bed B surface and to be unobtrusive and comfortable to the tactile senses of the patient P, regardless of where the patient P lies on the device 114. A flexible battery strip 16 and preferably but not necessarily, flexible and deformable control circuit 130 are preferably made as integral components of the device 114 along with a flexible, deformable sensor circuit 117, which will be described in more detail below. The control circuit 130 can have a variety of functions and capabilities, according to this invention, but the most important function is to produce output signals in the integral, flexible, electronic, sensing and control device 114 itself that are in a format useable in a conventional nurse call circuit C to actuate a nurse call monitor M without the need for any external interface or control components between the device 114 and a conventional nurse call circuit C access point W, other than a cord 32 or suitable wireless signal transmission system (not shown in FIG. 2). The access point W can be a conventional nurse call system wall socket or data input unit W, depending on whatever particular nurse call system is installed in a particular hospital or care facility. Such nurse call wall socket or data input unit W is not part of this invention. An on/off or start/stop switch 30 can be positioned in the cord 32 or directly on the integral, flexible, electronic, sensing and control device 114. The device 114 can be covered by a protective plastic or vinyl envelope or sheath 112, if desired, for sanitary purposes and to protect the circuit components of the device 114 from damage.

There are many ways that the sensing and control device 114 could be configured to sense the presence or absence of the patient P on the bed B, such as capacitive proximity sensors, micro-switches, and the like. This invention requires only that such patient P sensing device has a structure that is flexible, not obtrusive, and comfortable to the tactile senses of the patient P, so that it contributes to, and does not detract from, the overall non-obtrusive comfort and use of the integral, flexible, electronic, sensing and control device 114 of this invention. One such suitable sensor circuit 117, based on openable and closeable switch structures fabricated as electrically conductive traces 115, 115', 115" on juxtaposed flexible substrates 121, 122 held apart by compressible spacers 120, illustrated in FIGS. 4 and 5, existed prior to this invention, but is particularly adaptable to use as an integral part of this invention.

Figure 4:
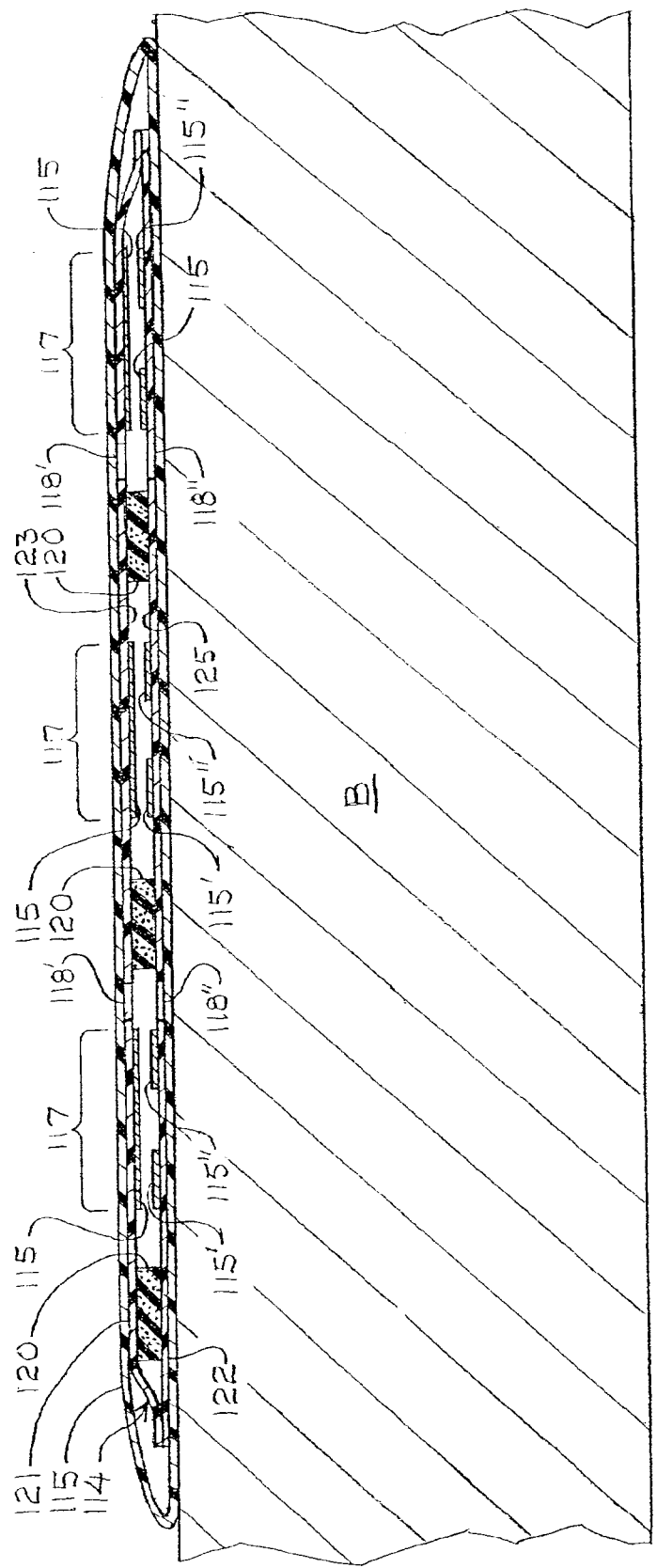
FIG. 4 is an even more enlarged cross-sectional view of the patient bed monitoring apparatus taken along section line 4—4 of FIG. 2 to illustrate its open circuit configuration.
Figure 5:
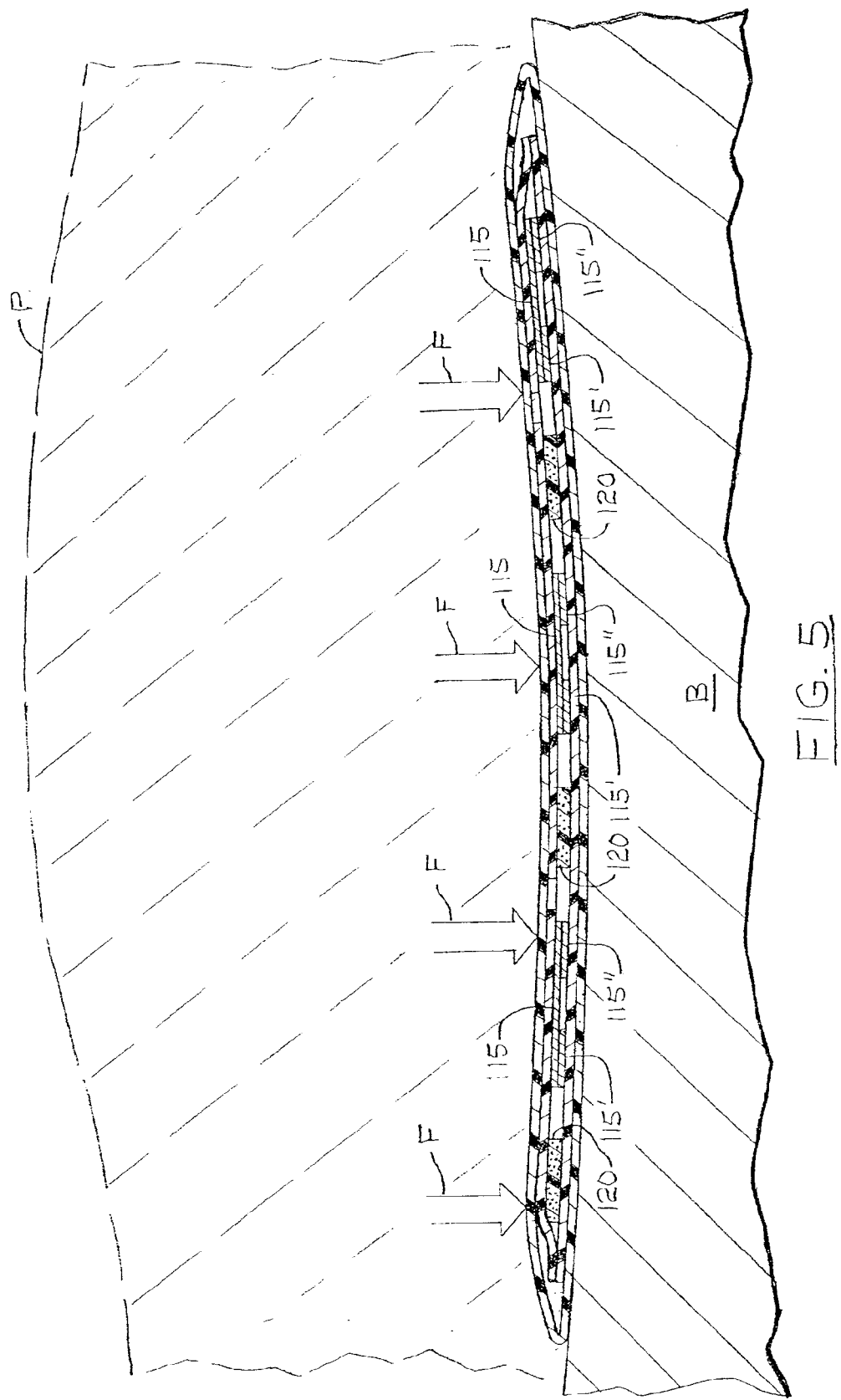
FIG. 5 is an enlarged cross-sectional view of the patient bed monitoring apparatus similar to FIG. 4, but taken along section line 5—5 of FIG. 2 to illustrate its closed circuit configuration due to weight of the patient positioned on the patient bed monitoring apparatus.

Essentially, as will be described in more detail below, the sensor circuit 117 shown in FIG. 4, where there is no patient weight on the sensor circuit 117, the inherent elastic memory of compressible spacers 120 keep the conductive traces 115 on the inside surface of the top substrate 121 separated from the conductive traces 115', 115" on the inside surface of bottom substrate 122. Therefore, an electric circuit comprising traces 115', 115" remains open so that no electricity can flow between traces 115', 115". However, as shown in FIG. 5, where the patient P is positioned on the sensor circuit 117, the force F of the patient's weight overcomes the inherent elastic memory of spacers 120 and compresses them until one or more of the top conductive traces 115 contact one or more of the bottom traces 115', 115" to complete the electric circuit between at least one trace pair 115', 115", i.e., to produce a closed circuit. The traces 115' and traces 115" are connected in parallel so that a closed circuit condition between any trace 115', 115" pair produces a closed circuit condition for the entire sensor circuit 117. Consequently, an open circuit 117 is indicative of the first condition, when the patient P is not positioned on any portion of the sensor circuit 114, while a closed circuit is indicative that the patient P is positioned somewhere on the sensor circuit 117, thus is positioned on the bed B.

As will also be explained in more detail below, the sensor circuit 117 is connected to the control circuit 130 FIG. 6, which includes a microprocessor or controller unit not shown in FIG. 2). The control unit in controller circuit 130 senses the presence or absence of an input signal front the sensor circuit 117, and, in response and according to certain timing criteria, the control unit generates an output signal on one or more conductors 32 (or on a wireless signal transmission system—shown in FIG. 2) for use in actuating a nurse call monitor M, such as an alarm, light, or other notification device and for use in recording patient movement information. An audible alarm (described below) responsive to the presence or absence of input signals from the sensor circuit 114 or responsive to an output signal of control circuit 130 can also be provided as part of the integral, flexible, electronic, sensing and control device 114, preferably by a piezoelectric element or other like element of control circuit 130.

As an example, the timing criteria in the control circuit 130 can be set to output a signal immediately upon sensing an input signal from sensor circuit 117, or it can be set to wait for some time interval, such as three seconds, before generating an output signal to the nurse call circuit C, indicating the absence of the patient P. The latter mode minimizes false alarms of patient P absence to the nurse call monitor M due to mere movement of the patient P on the bed B, such as by removing his or her weight only momentarily from the sensor 114. A longer or indefinite time setting, such as a "hold mode" or "sleep mode", may be intentionally selected by a care giver, for example, to allow enough time for a patient P to be escorted to a remote location, such as a toilet or an x-ray station, thereby removing his or her weight from the sensor 114, for an extended period of time without actuating the control circuit 130 to generate an output signal, or to conserve energy, especially to conserve on the internal battery power supply provided in some embodiments. The controller unit in the control circuit 130 can also be set, for example, to terminate the hold or sleep mode, and to terminate an output signal on conductor 32 when the patient P is back on the sensor 114. In some embodiments, the controller unit can also be set to terminate the hold or sleep mode and to terminate an output signal on conductor 32 for some fixed time period, such as 30 seconds or, alternatively, to continue the output signal, once it is actuated, until it is turned off by a health care professional.

The controller unit of control circuit 130 can, for example, receive external signals via the conductor 32, such as remote signals from programming connections (not shown in FIG. 2), or from computer operated nurse call systems or other computer operated monitoring systems to perform control unit functions, such as to turn off an output signal, to place the system in a hold or sleep mode, or to poll and access data stored in the controller unit of control circuit 130, such as date and time of first use, dates and accumulated hours of ongoing active monitoring, and dates and times of hold mode use, as will be explained in further detail below.

Further, the controller unit in control circuit 130 also senses and monitors movement and non-movement of the patient P. The presence or absence of intermittent, momentary, or periodic input signals from the sensor circuit 117 are sensed by the controller unit of circuit 130 control, and in response, and according to certain timing criteria, corresponding output signals are generated by the control circuit 130 on conductor 32 for use in actuating a nurse call monitor M, such as an alarm, light, or other notification device and for use in recording patient movement information. For example, the timing criteria in the controller unit can be set to output signals immediately upon sensing the presence of input signals from sensor circuit 117, or the controller unit can be set to wait for some time interval before generating output signals, each corresponding to patient P movement information. The controller unit, therefore, can monitor intermittent, momentary, or periodic movement of the patient P. As another example, the timing criteria in the controller unit can be set to output a signal after a time interval during which no input signal from the sensor circuit 117 is sensed by the controller unit. The controller unit, therefore, can monitor non-movement of the patient P. An audible alarm can be provided responsive to the input signals of the sensor circuit 117 or responsive to an output signal of control circuit 130, preferably by a piezoelectric element or other like element (not shown in FIG. 2).

The controller unit or microprocessor (processor 36 in FIG. 6) of control circuit 130 can be programmed with instructions or data, either by external signals via conductor or conductors 32, such as remote signals from the nurse station, or by programming connections (not shown in FIG. 2). Instructions or data may include initial settings, such as an output signal delay period, timer and clock data, and output signal, hold, or sleep instructions, as will be explained in further detail below.

The controller unit can receive an initial "wake up" or "start" signal, such as a signal generated by the weight of the patient P upon the sensor circuit 117 to complete a circuit 115', 115", or specifically, to provide a closed circuit condition or configuration, to generate an initial signal and thereby wake up or actuate the control circuit 130 to begin its sensing and monitoring functions. The initial signal may be provided as a grounded condition of the control unit, as further described below.

Further, the controller unit in the control circuit 130 can sense and monitor the energy level of an internal power source, such as the batteries in the flexible battery strip 16 shown in FIG. 2. A voltage, current, or other value indicative of the energy level of the batteries is sensed by the controller unit. The controller unit senses the electrical value, and in response and according to certain predetermined or programmed criteria, the controller unit generates an output signal on conductor or conductors 32 for use in actuating a nurse call monitor M, such as an alarm, light, or other notification device, for use in placing the controller unit in a hold or sleep mode, or both. An audible alarm can be provided responsive to the electrical value or responsive to an output signal of the control circuit 130, preferably by a piezoelectric element or other like element of the control unit (not shown in FIG. 2).

The control circuit 130 can also be placed in a hold or sleep mode by providing instruction to the controller unit, either by external signals via conductor or conductors 32, such as remote signals from the nurse station or other monitoring equipment, by programming connections, or, in some embodiments, by hand contact at some discrete location on the exterior of container or sleeve 12 corresponding with a switch or other signal component in controller circuit 130. Instruction for a hold or sleep mode stops the controller unit from monitoring for the presence, absence, or movement, or a combination thereof.

Figure 6:
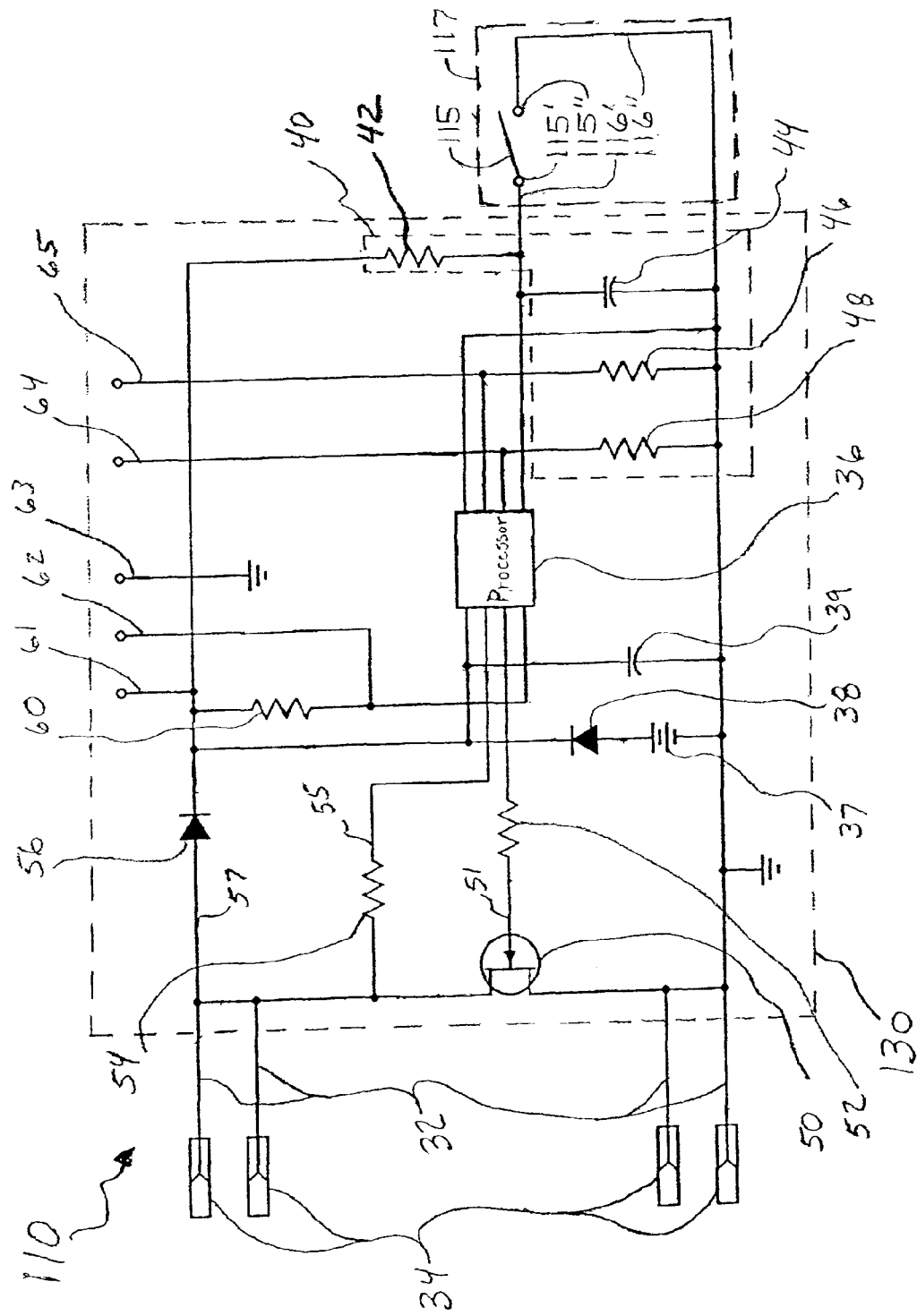
FIG. 6 is a schematic diagram of an electric circuit, including the sensor circuit and the control circuit, of the patient bed monitoring apparatus of FIG. 2.

An example electrical circuit for the sensor 114 is shown in FIG. 6, including the sensor circuit 117 and the control circuit 130. As mentioned above, the sensor circuit 117 should be flexible and able to conform along with the flexible substrates 121, 122 (FIGS. 4 and 5) to whatever shape or deformation the bed B surface has or undergoes as the patient moves on or off the sensor 114. It is also desirable, but not essential, that the control circuit 130 also has flexible or otherwise conformable circuit components that can be made or are available in flexible embodiments. Such flexible or conformable components can comprise inked, etched, deposited, or otherwise formed traces and components flexible or on a conformable base material suitable to serve as a circuit board or substrate, such as plastic or vinyl. If the control circuit 130 is not made with such flexible or conformable components or is not fabricated on a flexible or conformable base material, it should at least be made as small as practical or feasible so as to interfere as little as possible with the overall flexibility and ability of the sensor 114.

Figure 7:
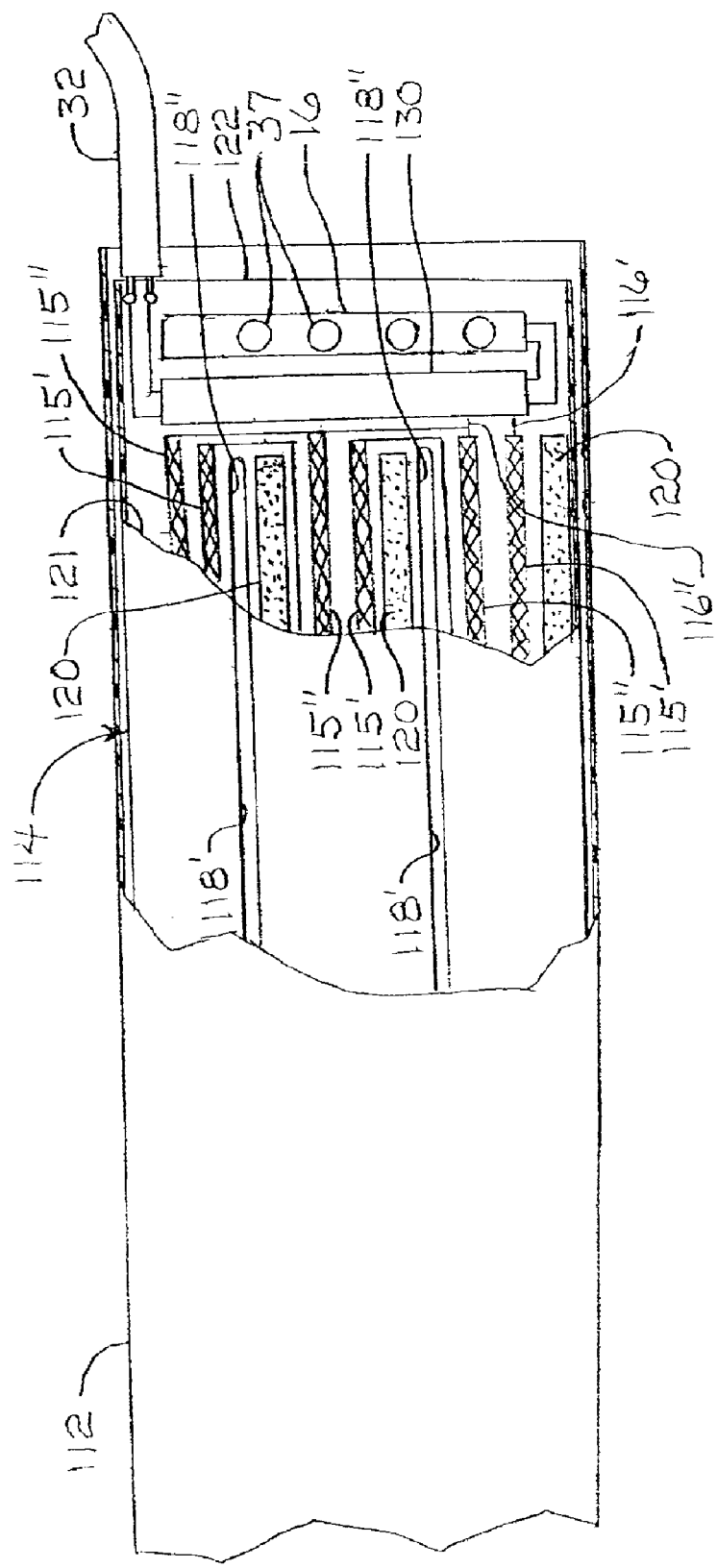
FIG. 7 is an enlarged top plan view of the right end of the patient bed monitoring apparatus of FIG. 2 with a portion of the sheath and a portion of the top substrate cut away to reveal the circuit and other components.
Figure 8:
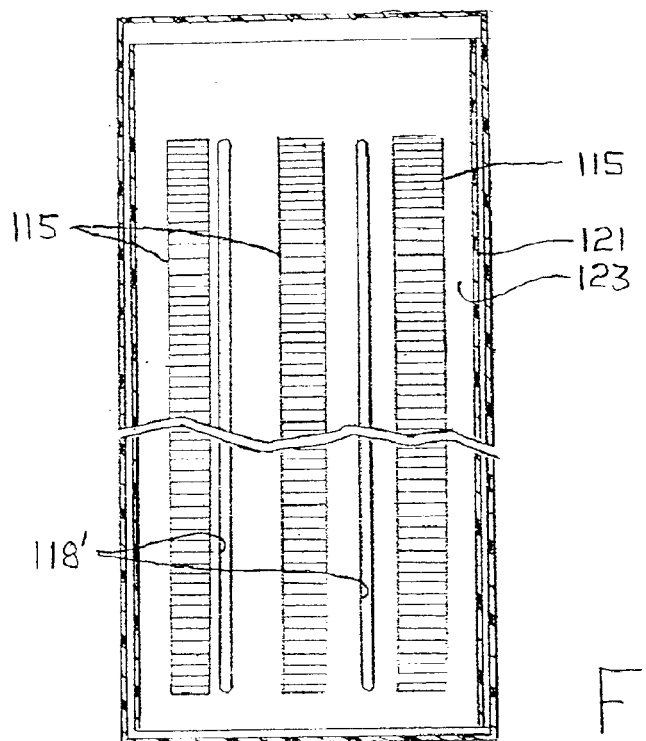
FIG. 8 is a bottom plan view of the sensor and control circuit components on the top substrate taken as a cross-section view of the patient bed monitoring apparatus along section line 8—8 in FIG. 3.
Figure 9:
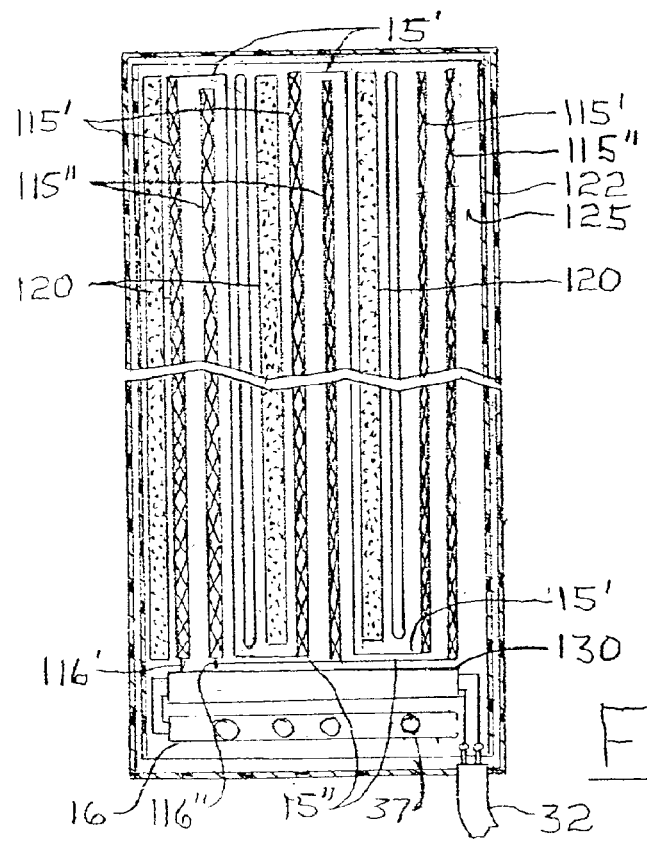
FIG. 9 is a top plan view of the sensor and control circuit components on the bottom substrate taken as a cross-section view of the patient bed monitoring apparatus along section line 9—9 in FIG. 3.

As shown in FIGS. 6 and 7, the sensor circuit 117 is connected to the control circuit 130 by one or a plurality of connections 116, 116'. Connections 116, 116' may be any known connection or connections that allow signal communication between the sensor circuit 117 and the control circuit 130, but are preferably flexible and conformable to deformation, such as inked, etched, deposited, or otherwise formed traces, or the like.

As mentioned above, the sensor circuit could be provided in any of a number of ways, but the preferred open/close switch configuration formed by flexible and conformable conductors on flexible and deformable plastic or vinyl sheets or substrates 121, 122 are illustrated in FIGS. 4–5 and 7–9.

Essentially, the sensor device 114 has a top conformable base 121 and a bottom conformable base 122, which conform in shape and contact with regard to a patient support surface or surfaces of the application to which the system is being provided, a patient bed. The top base 121 is used as a top substrate on which the flexible and conformable sensor circuit components 115 are mounted or deposited, and the bottom base 122 is used as a bottom substrate on which the flexible and conformable sensor circuit components 115', 115" are mounted or deposited. Such circuit components are preferably deposited as conductive traces on the respective inside surfaces 123, 125 the top base 121 and bottom base 122, respectively. The several circuit components 115' on bottom substrate 122 are connected together electrically by conductors 15', and the several circuit components 115" are connected together electrically by conductors 15". Therefore, when any portion of the circuit components 115 on the top substrate 121 connect together any portions of both circuit components 115' and 115" on the bottom substrate 122, the entire sensor circuit 117 is in closed circuit condition. The connecting conductors 15', 15" are also preferably flexible and conformable inked, etched, deposited, or otherwise formed traces, as explained for other circuit components.

The electrical circuit of FIG. 6 can be implemented by a combination of circuit components, some of which are printed on inside surfaces 123, 125 of top and bottom substrate 121 and 122, respectively. As explained above, when the inside surface 123 of the top substrate 121 overlays and interfaces with the inside surface 125 of the bottom substrate 122, the circuit components on each conformable substrate 121, 122 interact with each other in response to weight of a patient P, creating a closed switch configuration, as previously described and as will be described in further detail below.

During use, the weight of a patient P forces the components of the electrical connections 115 of the top substrate 121 into contact with components of the electrical connections 115', 115" of the bottom substrate 122 to form a closed connection, thus a closed switch configuration of sensor circuit 117. With sensor circuit 117 in a closed switch configuration, it indicates the presence of the patient P, movement of the patient P, or both, as described in further detail below. If the weight of a patient P is removed from the sensor 114, such that electrical contact between electrical connections 115 of top substrate 121 and electrical connections 115', 115" of bottom substrate 122 is prevented, the sensor circuit 117 will be in an open switch configuration and an input signal will be detected in the control circuit 130. Such open circuit configuration of system 110, and the input signal detected by control circuit 130, indicates the absence of the patient P, while a momentary, intermittent, or periodic open circuit configuration may indicate movement of the patient P, or both, as described in further detail below. Only one or a portion of electrical connections 115 of top substrate 121 need contact one or a portion of electrical connections 115', 115" of the bottom substrate 122 to provide a closed switch configuration.

The elongated slots or holes 118' and 118" in the top and bottom bases 121, 122, respectively, allow the sensor device 114 to conform within sleeve 112 to uneven or flexed bed surface or other patient surfaces, as previously described, without wrinkling or binding.

As also explained above, the electrical components 115 on the top substrates 121 and the electrical components 115', 115" on the bottom substrate 122 are flexible, bendable, or otherwise conformable, and they are held apart in an elastic, yieldable manner by at least one compressible or yieldable support element, and in preferred embodiments, by resilient, squeezable, deformable or otherwise conformable spacers 120. The spacers 120 have an inherent elastic bias or memory that can easily separate the substrates 121, 122 and respective circuit components 115 and 115', 115", when there is substantially no external weight or force on the sensor 114. However, the weight of a patient P on the sensor 114 readily overcomes the inherent bias or memory of the spacers 120, which yield or otherwise conform and allow the substrates 121, 122 to collapse together, which causes at least one of the circuit components 115 of the top substrate 121 to contact and connect electrically at least one component pair 115', 115" on the bottom substrate 122 to close the circuit 117. While not shown, persons skilled in the art understand that the present invention can also be implemented with a normally closed switch configuration for sensor circuit 117, which opens to an open switch configuration in response to the applied weight of a patient, thereby reversing the input signals directed to the control circuit 130 from those described above. Modifications, programming or logic for system 110, including those for controller 36 in control circuit 130, to perform the same functions as provided for the preferred embodiments herein may be easily implemented by persons skilled in the art for such an alternative embodiment, and thus are considered to be within the scope of the present invention.

As mentioned above, sensor circuit 117 may be provided in configurations other than the preferred configurations shown and described above, but still consistent with the present invention. Accordingly, sensor circuit 117, and especially the electrical components and connections 115 and 115', 115" may be provided in other configurations that provide for the indication of the presence, absence, or movement of the patient P, and in some embodiments, provide for open and closed circuit configurations, and in preferred embodiments, open and closed switch configurations. For example, but not by way of limitation to the present invention, the electrical connections may be provided in a network of connections, in a series of substantially parallel network of connections, in a substantially intersecting network of connections, or in any combination of configurations and topologies that allow for both open and closed switch capability of on-off device 17, and both open and closed circuit capability of the system.

As previously described, the electrical circuit shown in FIG. 6 is comprised of a sensor circuit 114 and a control circuit 130, and further having output connections 32. At least one output connection is provided to allow electrical flow, especially signal flow, to and from control circuit 130 and may comprise a cable, wire, conductor, lead, plug conductor, or other electrical connection and can be flexible or otherwise conformable circuit components of system 110, such as the conductors, circuit connections, and other circuit components of the sensor circuit 114 and control circuit 130, and in some embodiments, inked, etched, deposited, or otherwise formed output connections, and can be provided on a conformable base material suitable to serve as a circuit board or substrate, as previously described. In some embodiments, plug conductors 34 facilitate connection with conventional nurse call circuits C (FIG. 2) or other monitoring equipment. In some embodiments, four-plug conductors and corresponding output connections may be needed for compatibility with conventional nurse call circuits C. However, two, a plurality, or no plug conductors may be provided in accordance with the present invention.

Figure 10:
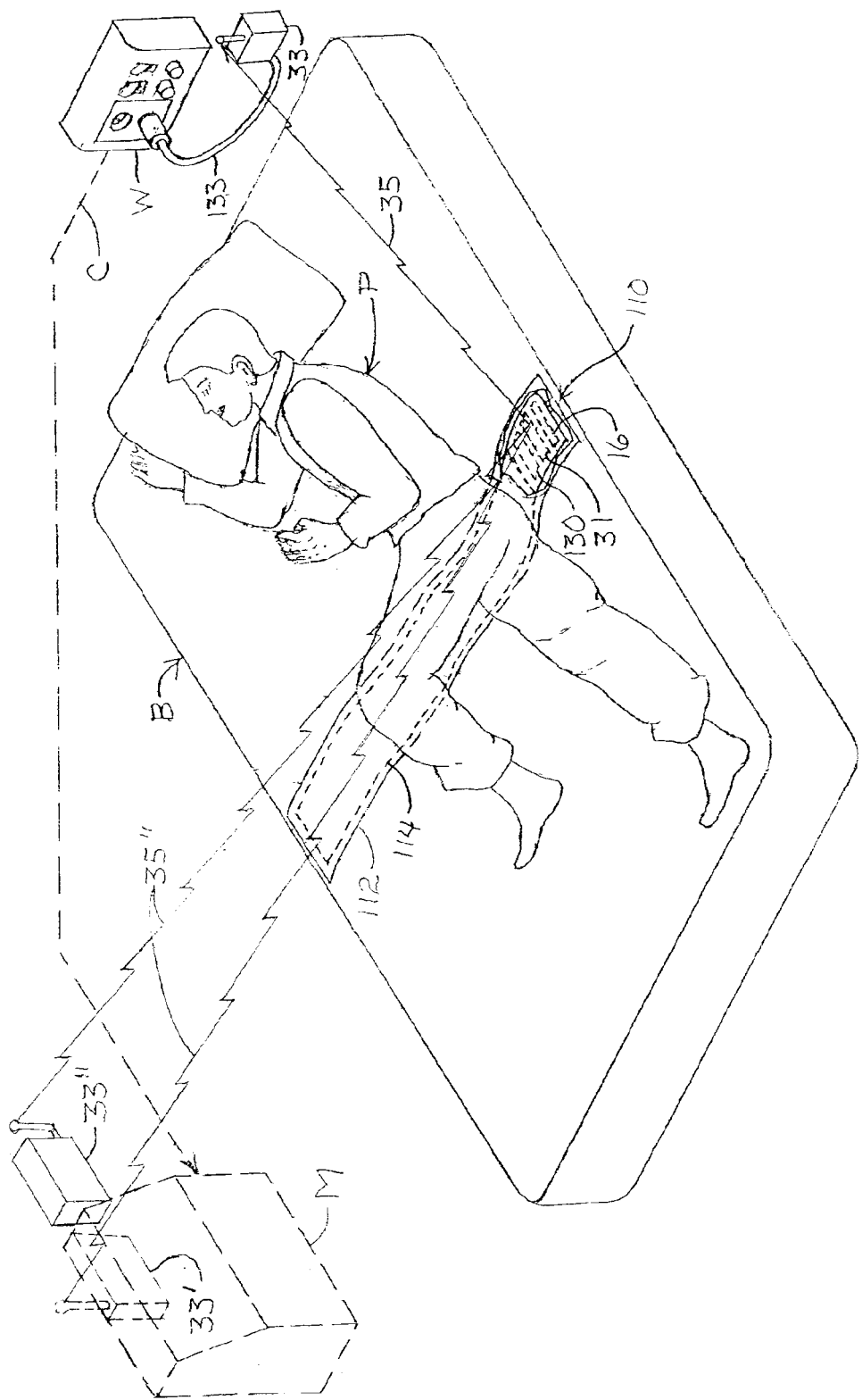
FIG. 10 is a perspective view of a wireless transmission embodiment of the patient bed monitoring apparatus of this invention.
Figure 11:
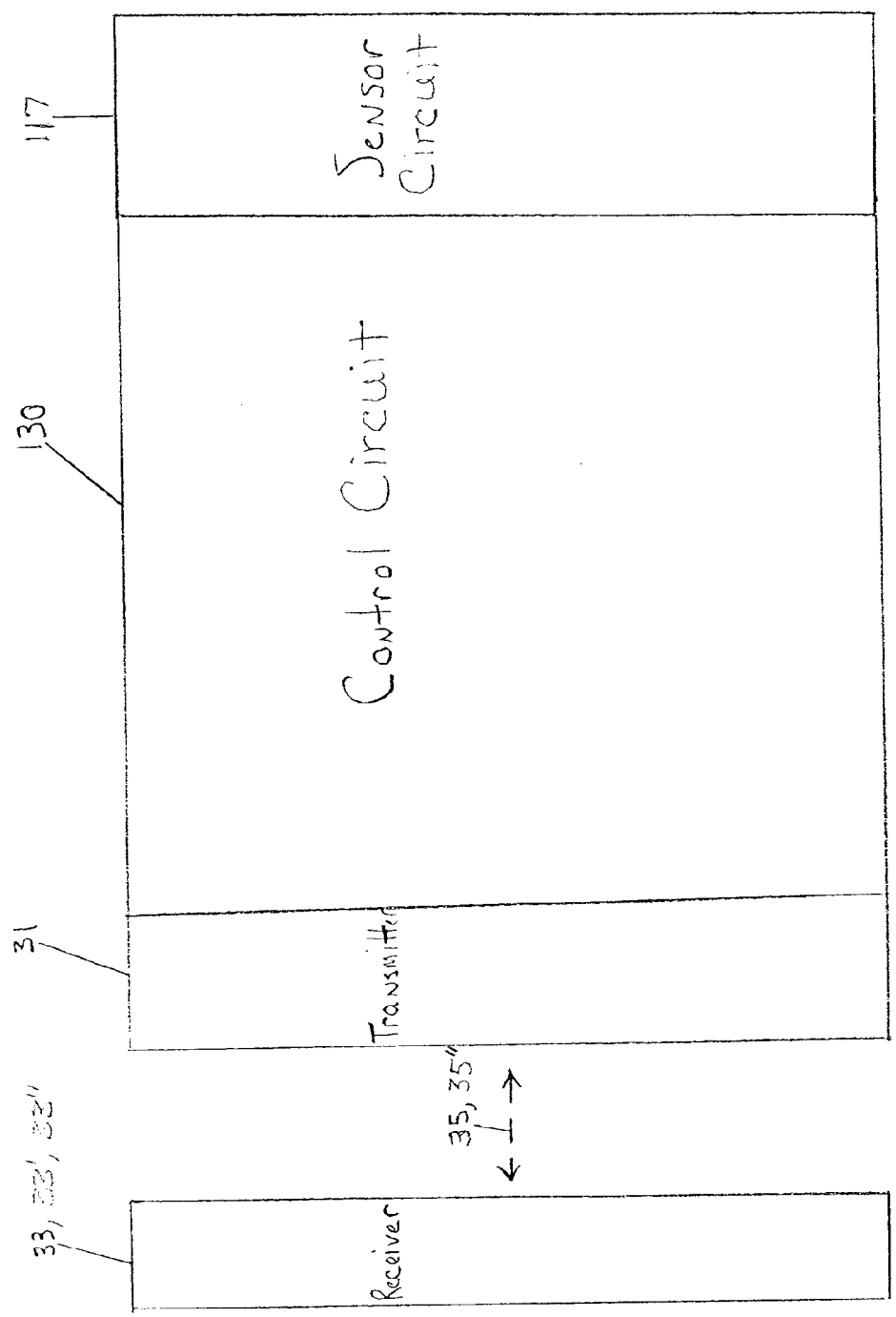
FIG. 11 is a function block diagram of the wireless embodiment of FIG. 10.

Embodiments of the monitoring system 110 can also have a wireless connection rather than or in addition to, hardwire connections 32, to a wireless receiver or receivers, such as the wireless receiver 33, 33', or 33" as illustrated in FIGS. 10 and 11. The in-room receiver 33 depicted in FIG. 10 can be positioned in an out-of-the-way position and connected, for example., by a cord 133, into the wall receptacle W or other connecting point of a nurse call circuit C or other monitoring equipment. If the remote nurse call monitor M is equipped with a wireless receiver 33', as illustrated in FIG. 10, the in-room receiver 33 may not be necessary. Still another option is a stand-along, remote wireless receiver 33" located, for example at a nurse station, but which is not necessarily a part of, or connected to, the conventional or institutional nurse call monitor M. Such a stand-alone, wireless receiver 33" can have visual, audio, or other alarm or notification features to activate in response to wireless signals from a transmitter 31 in the flexible, electronic, sensor and control device 114. In fact, the stand-alone, wireless receiver 33" can be configured to receive, process, and identify signals 35" from a plurality (not shown) of electronic sensor and control devices 114, especially where the signal 35" from each device 114 is encoded with a unique identification code that is different from the signals 35" from other devices 114 (not shown). The receiver 33" can then have a display that identifies the particular one of the plurality of devices 114 that is transmitting a signal 35". Such uniquely encoded signals 35" may also be identifiable by the receiver 31' that is part of the nurse call monitor M. Many transmitters 31 suitable for this application are available commercially, for example, an Inovonics™ RF transmitter obtainable from Inovonics™ of Louisville, Colo., U.S.A., such as the Inovonics™ Model No. FA241XS. The wireless transmitter 31 is responsive to the control circuit 130, providing signal transmission 35 through wireless signal transmission, and in preferred embodiments, wireless radio frequency (RF) transmission in the 900 MHz range, and in some embodiments, RF transmission between about 902 and 926 MHz. Microwave, infrared, or other wireless signal transmission techniques could also be used. Accordingly, output from the control circuit 130 can be provided through wireless connection for signal transmission, such as, in preferred embodiments, by wireless RF signal transmission or other wireless signal transmission, to one or more receivers 33.

The wireless transmitter 31 is an optional part of the patient sensing and monitoring system 110. Some embodiments of the present invention may have one or more receivers as part of the patient sensing and monitoring system 110. In some embodiments, the patient sensing and monitoring system is self-contained as to the wireless transmitter, as shown in FIG. 10, comprising the transmitter 31 as part of a single, enclosed unit with regard to the elements, components, devices, and apparatus that comprise the system 110, either substantially or entirely encompassed by container or sleeve 112, while allowing for wireless signal transmission as previously described. However, some embodiments of the present invention may alternatively have the wireless transmitter as an external component to system 110. The transmitter 31 is in electrical connection with control circuit 130, such as hardwire connection or as a component, element, device or apparatus of control circuit 130, allowing signal communication to and from control circuit 130. Embodiments of the present invention, therefore, may comprise a transmitter/receiver 31 that allows wireless signal communication to the control circuit 130, the communicated signals including external signals comprising programming instruction and other data, as will be further described below. Furthermore, the transmitter 31 may be a component, element, device or apparatus provided with a base or substrate 121 or 122 of the present invention, as previously described.

Preferred Circuit Embodiments

Referring now to the circuit diagram of FIG. 6, sensor 14 may provide for open and closed circuit configurations that signal the presence, absence, or movement of the patient, generating one or more input signals to the control circuit 130 as described above. Specifically, in an open switch configuration of sensor circuit 117, the resistor 42 will 'pull up' the voltage on the connected pin of processor or controller unit 36, such as to a voltage of 5 volts, such that substantially no voltage drop occurs over resistor 42 and substantially no current flows to processor 36, indicating the absence or movement of the patient as an input signal. The input signal may be a change in voltage or a change in current, such as the change from a voltage drop across resistor 42 to substantially no voltage drop and substantially no current flow to processor 36, or other types of electrical signals sensed by processor 36, and control circuit 130, generally. In a closed switch configuration of on-off device 17, the connected pin of processor 36 will be electrically shorted to ground, providing a voltage drop across resistor 42 and current flow to processor 36, indicating the presence or movement of the patient. Therefore, the input signal to control circuit 130 indicating the absence or movement of the patient, such as a change in voltage or current, occurs depending upon the open or closed circuit condition of sensor circuit 117.

The electrical circuit of FIG. 6 comprises a control circuit 130 having a signal conditioner 40. Signal conditioner 40 provides for the removal of static and transient signals from signals generated by sensor 114 and further is responsive to and alleviates switch bounce and other adverse affects resulting from undesired current flow or non-flow from the sensor. Switch bounce may occur during the opening or closing of the sensor circuit 117, resulting in a series of opened and closed circuit conditions and the resulting series of undesired signal generation. Signal conditioner 40 filters current from the sensor 114 of static and transient signals, noise, switch bounce, or other undesired effects. Signal conditioner 40 may especially provide for the supply of input signals, such as changes in voltage, representing an open or closed configuration of sensor circuit 117, and in preferred embodiments, allows such input signals to be received by processor 36 if a closed circuit configuration is maintained for a predetermined amount of time. Preferred embodiments provide signal conditioning circuitry as the resistors 42, 46, and 48 and capacitor 44 configuration shown in FIG. 6. Other filters and topologies may be readily provided in accordance with the present invention to achieve a signal conditioning feature.

Furthermore, control circuit 130 has control and processing capability, and in some embodiments, programmable control and processing features. In reference to the embodiment of FIG. 6, control circuit 130 comprises a controller unit or processor 36. Furthermore, the control circuit 130 can be comprised of instructions that are stored on at least one storage media (not shown). The instructions and other data can be programmed or otherwise entered by a user through at least one input connection, and in some embodiments a plurality of input connections, such as programming connections 61–65 or externally through conductor or conductors 32, and retrieved and executed by the processor 36. The instructions and other data can also be programmed or otherwise entered, in some embodiments, by external signals, such as remote signals from the nurse station or other monitoring systems, via conductors 32 or through wireless transmission provided by a transmitter 31 capable of transmitting received signals to the control circuit 130, as previously described. Instruction or data may include initial settings, such as an output signal delay period, timer and clock data, and output signal, hold, or sleep instruction. The processor 36, in preferred embodiments, provides timer and clock features and functions, as further described below.

Programming connections 61–65, and in some embodiments conductor 32 or a wireless transmitter and receiver 31, allow the entry of instructions and data, such as a location identifier, and in some embodiments a bed identifier or number, clock and timer data and instruction, alarm data and instruction, hold and sleep instruction, and the like, and as further described below in accordance with the present invention. Programming connections, in preferred embodiments, comprise conductive touch pads for system and processor programming and control. Memory capability is preferably provided by memory devices such as read-only (ROM) and random access memory (RAM), and may comprise in some embodiments 100 bytes of ROM and 15 bytes of RAM, and in preferred embodiments, 1000 bytes of ROM and 256 bytes of RAM.

A battery or plurality of batteries 37, preferably mounted on a flexible strap 16 (FIGS. 2 and 7), as described above, or alternatively an external power supply, is provided to power the system 10. In the preferred embodiments, each battery 37 may be, for example, 3 volt lithium batteries 37. The life of the battery, in some embodiments, may provide for a disposable system 110. A disposable patient sensing and monitoring system 110 may allow a short service life, potentially a service life of several weeks, or may provide a system that has a longer service life, potentially at least one year of service life or more, depending upon the application requirements of the system and the type of power supply. High-usage applications, such as a patient sensing and monitoring system 110 used for patients having frequent periods of activity, may reduce the battery 37 life and the system service life. An isolation element, such as diodes 38 and 56 in FIG. 6, electrically isolate the control circuit 130, and especially the battery 37, from electrical effects external to system 110. A power supply filter, and in preferred embodiments capacitor 39, filters output from the power supply to accommodate for current or voltage spikes or other undesirable power supply effects.

Embodiments of the present invention provide a patient sensing and monitoring system 110 that transmits an output signal depending on the open or closed configuration of sensor circuit 117. Some embodiments may further provide an alarm, a data transfer feature, or both, that allows data or instruction, including but not limited to alarm data, to pass to and from the system 10 to external elements, such as the nurse monitoring circuit or other monitoring equipment, wireless receivers, or the like. According to one embodiment, resistors 52 and 54 and Field-Effect Transistor 50 provide such alarm and data transfer capabilities. The FET provides a switching feature to activate an alarm function, as further described below. The resistors 52 and 54 provide a data connection from processor 36 to external elements for data communication. Piezoelectric elements may also be provided, and can be self-contained with regard to system 10, to allow for an audible alarm sound.

Numerous modifications and combinations of the patient sensing and monitoring systems and the circuit embodiments disclosed will readily occur to those skilled in the art, such novel embodiments encompassed by the present invention, and it is not desired to limit the invention to the exact circuit construction and process shown and described above.

For example, the present invention would encompass a configuration having other circuit topographies, potentially including other circuit components or combinations of circuit components, including analog or digital circuitry, and embodiments providing software or firmware features, to accomplish the various functionality and features of the present invention. Circuit components, such as elements, devices, and apparatus of the sensor 114 and control circuit 130, can be provided by inked, etched, deposited, or otherwise formed traces, conductors, circuit connections, and other circuit elements, such as sensor circuit 117 and the circuit components of control circuit 130.

Furthermore, instructions can be provided as software, program code, and firmware or some other form of processing instructions, firmware including, but not limited to, program logic provided by one or a plurality of elements or devices, such as read-only memory. Some examples of storage media are memory devices and integrated circuits, or electrical components thereof. The instructions are operational when executed by the processor to direct the processor to operate in accordance with the present invention and as further described below. Those skilled in the art are familiar with instructions, processors, and storage media. The processor could comprise a microprocessor, logic circuit, or some other processing device. The processor could be distributed among multiple processing devices.

Figure 12:
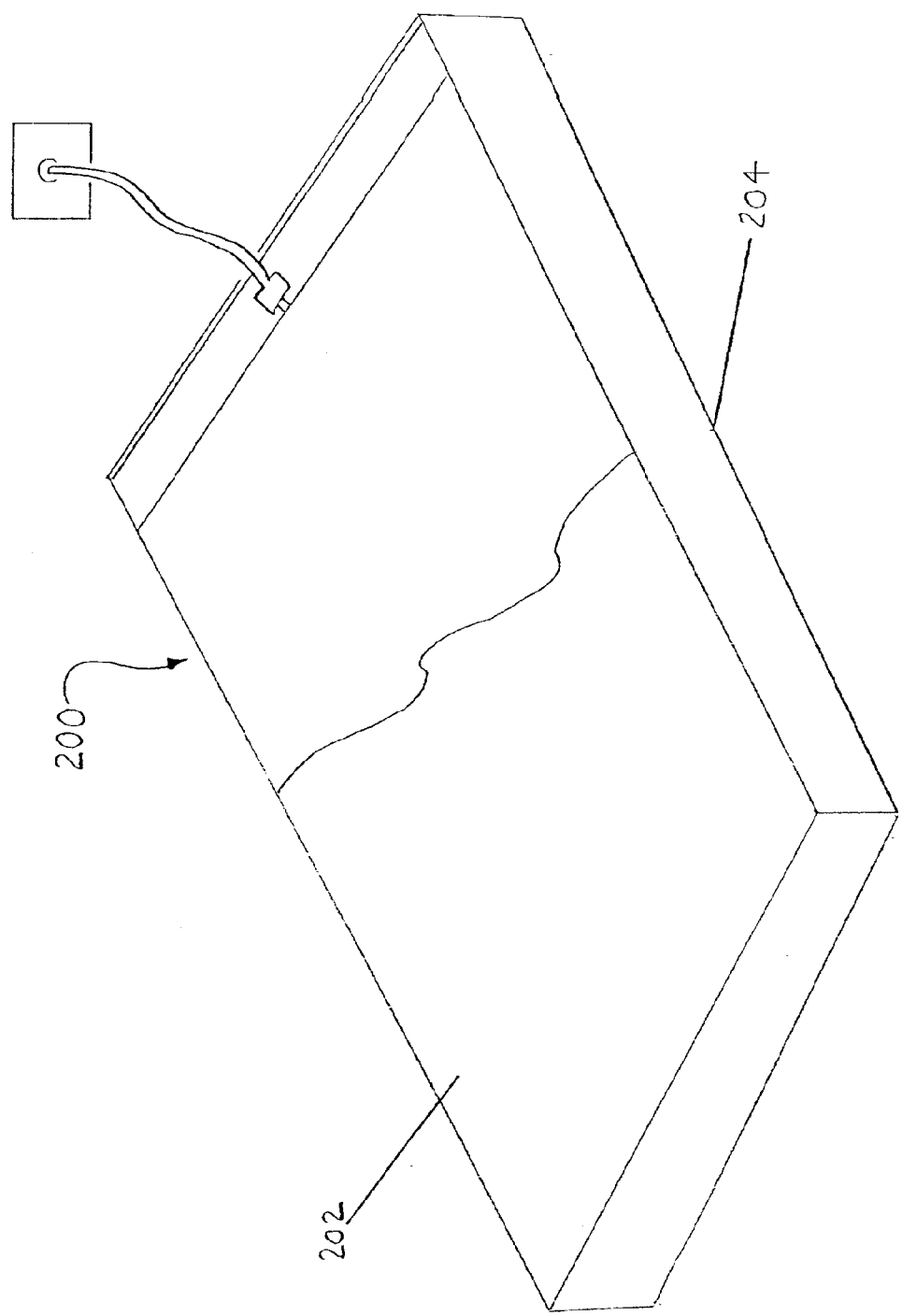
FIG. 12 is a perspective view of an alternate embodiment of the patient sensing and monitoring system of this invention in a mattress covering or pad configuration.

The embodiment of FIG. 2 may be used for other applied applications such as a chair, wheelchair, or other configurations, and can be provided to encompass the whole or any part of the bed or other patient support surface or surfaces. The surface may also be substantially adjacent the patient. For example, the patient sensing and monitoring system of the present invention may be preferentially configured: to cover a mattress surface, covering the entire surface, a substantial portion of a surface, or a portion thereof, such as a surface adjacent to the patient; in a mattress covering that is either removable or that is provided as a fixed surface of the mattress; as a component of the mattress; or other bed, chair, wheelchair, or other structural configurations. One such embodiment is shown in FIG. 12, wherein the patient sensing and monitoring system 200 is provided in a mattress covering or pad 202 of mattress 204. The mattress covering or pad 202, in some embodiments of the present invention, may be a fixed surface of the mattress. The patient sensing and monitoring system 200 may also be provided as a component of the mattress.

The embodiment of FIG. 2, as well as other embodiments, may be variously configured and still maintain the desired functionality of the present invention and the various features disclosed, including all features or a combination thereof. The present invention, furthermore, may also be preferentially configured to other applications, such as a chair, wheelchair, or other configurations. An embodiment of a patient sensing and monitoring system 300 in accordance with the present invention preferentially configured, as shown in FIG. 13, to a conventional chair or wheelchair 302. The patient sensing and monitoring system of the present invention may be preferentially configured to cover a chair surface or surfaces, covering the entire surface, a substantial portion of a surface, or a portion thereof. The surface may be substantially adjacent to the patient, for example, but not limited to, a surface of the seat, the backrest, or both, and may be provided in a chair covering or pad 304 that is either removable or that is provided as a fixed surface of the chair.

The present invention may further be provided in various dimensions, shapes and sizes to fit a particular configuration of an application, such as rectangular or strip, square, circular, triangular, polygonal, or any symmetrical or asymmetrical form. For example, other container elements may be provided, in various configurations, consistent with the present invention.

Sensing and Monitoring the Patient

Figure 14A:
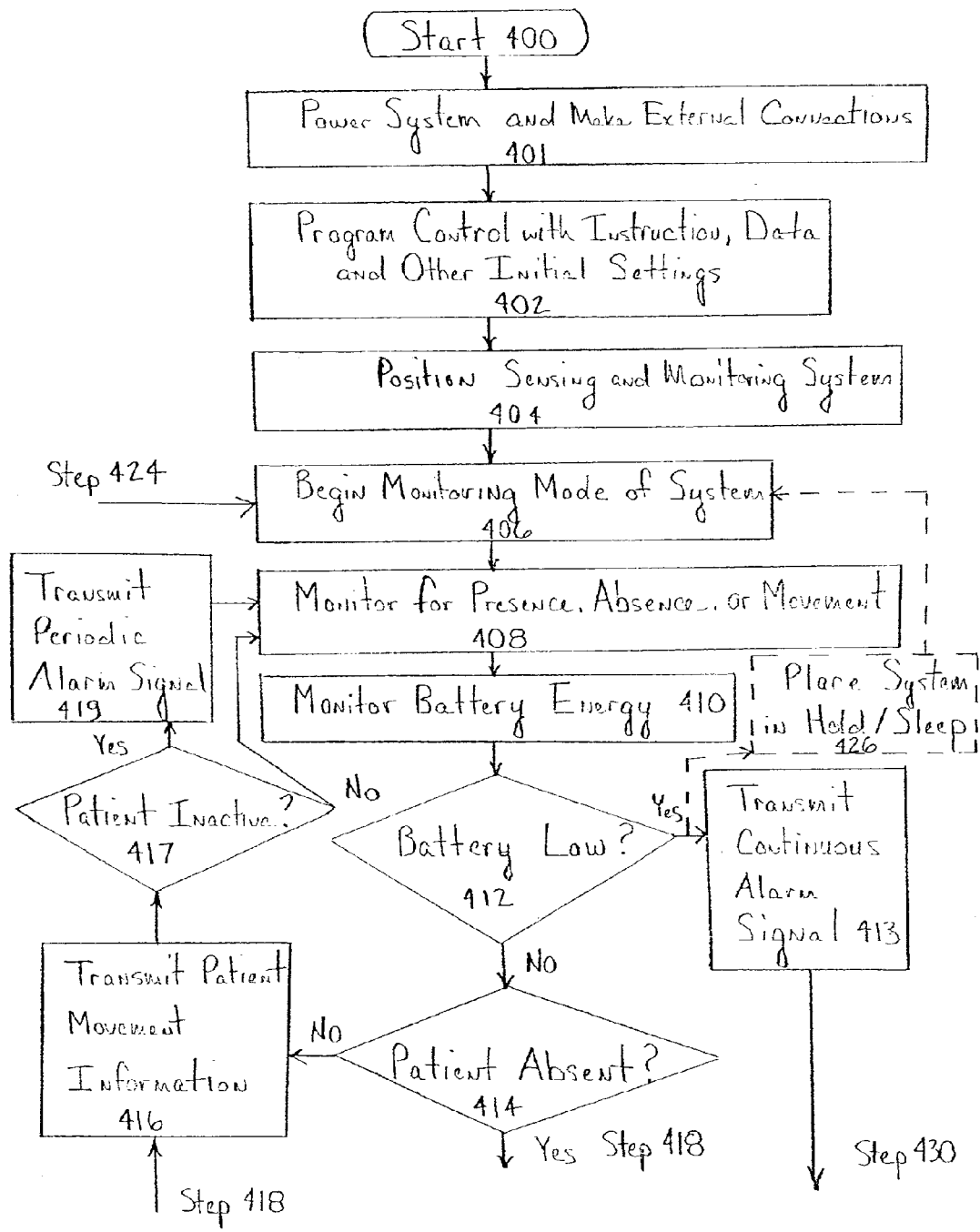
FIG. 14a is a flow chart illustrating programmable control features in accordance with one embodiment of the present invention.
Figure 14B:
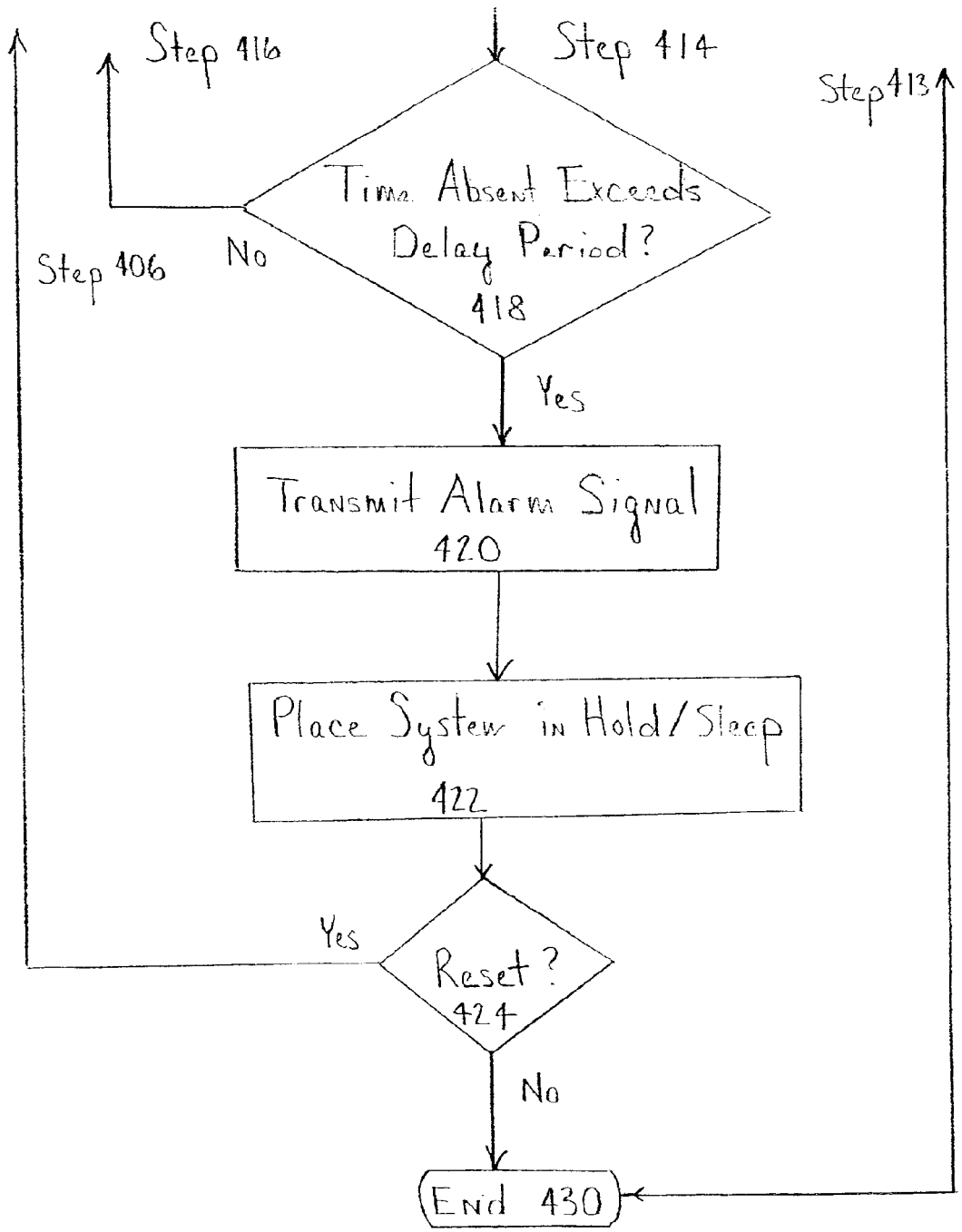
FIG. 14b is a continued flow chart corresponding to FIG. 11a illustrating programmable control features in accordance with one embodiment of the present invention.

One process for the sensing and monitoring of a patient in accordance with the present invention is provided in the flow chart of FIGS. 14a and 14b. The system is connected with the nurse call circuit or other monitor equipment, through hardwire connection or wireless connection as previously described, or otherwise configured for sensing, monitoring, and communicative operation 401. Powering of the system may be accomplished through an external power supply or through an internal power source. An "on" function of the control circuit 130, such as a signal provided through one or a plurality of input and/or programming connections 61–65 to control circuit 130 can be used to "wake up" or "start" control circuit 130. In preferred embodiments, the controller unit or processor 36 can sense an initial closing or other actuation of the sensor circuit 117 and, in response, will "wake up" or "start" the control circuit 130. The connection of the system 110 to external equipment may include cable, wire, lead, or other hardwire connection, such as plug conductors 34, or may include configuration of the wireless transmitter 31 to a corresponding receiver or receivers 33, or to a wireless capable nurse call circuit. (For the remainder of this description, reference to the system 110 includes the alternates 20, 300, and other variations covered by the invention.) The control unit 30 is then programmed 402 with instruction, data, or both, which may include a delay period and other initial settings, such as timer and clock data, hold or sleep instruction, as previously described. The system 110 is positioned 404 for the particular application, such as a bed, chair, wheelchair, or the like, as depicted in FIGS. 2, 12, or 13, and as previously described.

A monitoring mode for patient sensing and monitoring system 110 is initiated 406. Embodiments of the present invention provide activation of the monitoring mode of control circuit 130, such as through operation of processor 36, and other elements of system 110 by a first input signal to control circuit 130, generated by a closed circuit configuration of the control circuit 130 and sensor circuit 117. The weight of the patient actuates the sensor circuit 117 as previously described, as the patient is first placed upon the sensor 114. The assisting health care professional would ensure that the patient is placed upon the sensor 14 to provide an input signal to control circuit 130 to begin the monitoring mode of control circuit 130.

The system 110 then begins to monitor 408 for the presence, absence, and movement of the patient, monitoring for an input signal, so as to determine if an open or closed circuit configuration exists through the present configuration of sensor circuit 117. If the patient is subsequently absent from the system 110, and in preferred embodiments, the patient's weight is removed from the sensor 114 such that an open configuration is created of sensor circuit 117, as in an open circuit configuration of system 110, which functions to provide an input signal to the control circuit 130, the control unit will sense the input signal from the sensor circuit 114, the open circuit configuration of system 110, generally, and the absence of the patient 414. The determination of the absence of a patient may occur at predetermined or programmed time intervals, as previously described. The control circuit 130 generates an output signal for use in actuating a nurse call circuit or other monitoring equipment, such as an alarm, light, or other notification device, for use in recording patient movement information.

As an example, the timing criteria in the control circuit 130 can be set to output a signal immediately upon sensing the absence of an input signal from sensor 114, or it can be set to wait for some time interval, such as three seconds, before generating an output signal to the nurse station or other monitoring equipment corresponding to the absence of the patient. The latter mode minimizes false alarms of patient absence to the nursing station or other monitoring equipment from mere movement by the patient, whom might remove his or her weight only momentarily from the sensor 114. A longer or indefinite time setting, such as a "hold mode" or a "sleep mode", may be intentionally selected by a care giver, for example, to allow enough time for a patient to go to a remote location, such as a toilet or x-ray station, and return without actuating the control unit 30 to generate an output signal, or to conserve energy, especially to conserve on the internal power supply provided in some embodiments, as previously described. The control unit can also be set, for example, to terminate the hold or sleep mode, also previously described.

In some embodiments of the present invention, and during the monitoring 408 of the patient, the control circuit 130 concurrently monitors 410 the energy level of an internal power supply, such as battery 37. If the control circuit 130 determines 412 battery energy level is below a predetermined, and in some embodiments programmed, threshold amount, control circuit 130 will cause an output signal to be generated. The signal can actuate an alarm, such as an intermittent "chirp" sound and/or send a "low battery" signal to the nurse call monitor M or wireless receiver 33, 33', 33" described above, which preferably is configured or programmed to identify such a "low battery" signal and, in response, to actuate an appropriate display or alarm 413 to notify nurse personnel of the low battery condition of that particular device 114. In some embodiments, an audible alarm signal will be generated by a provided piezoelectric element or other such device, provided as a self-contained element with regard to system 110 in some embodiments. The system 110 may then be replaced or power supplied by an external source. In some embodiments, control circuit 130 can initiate a hold or sleep mode 426, conserving power of battery 37.

Determining the absence of the patient 414 is followed or concurrently determined with the transmission of patient movement information 416 to the external nurse call circuit, receiver or receivers, monitoring equipment, or the like. Input signals are provided to control circuit 130 if a closed configuration of sensor circuit 117 exists during monitoring 408. The presence or absence of intermittent, momentary, or periodic input signals from the sensor circuit 117 are sensed by the controller unit of circuit 130, and in response, and according to certain timing criteria, a determination of patient inactivity is made 417, and corresponding output signals are generated by the control circuit 130 on conductor 32 for use in actuating a nurse call circuit C or other monitoring equipment such as an alarm, light, or other notification device 419 and for use in recording patient movement information.

For example, the timing criteria in the control circuit 130 can be set to output signals immediately upon sensing input signals from sensor 114, or the control circuit 130 can be set to wait for some time interval before generating output signals, corresponding to patient movement information. The controller unit or processor 36 in control circuit 130 may be programmed to count a number of input signals corresponding to a closed configuration of sensor circuit 117 and the presence of the patient and transmit the number of input signals during a period of monitoring, corresponding to movement or non-movement of the patient, and the level of activity of the patient. The control circuit 130, therefore, can monitor intermittent, momentary, or periodic movement of the patient, which may indicate an inactive status of the patient. As another example, the timing criteria in control circuit 130 can be set to output a signal after a time interval during which no input signal from the on-off device of sensor 114 is sensed by the control circuit 130. The control circuit 130, therefore, can monitor non-movement of the patient. An output signal, and in preferred embodiments a periodic alarm signal, may be transmitted 419 to the nurse call circuit, receiver or receivers, monitoring equipment, or the like, during the period of inactivity. An audible alarm can be provided responsive to the input signals of the on-off device or responsive to an output signal of control circuit 130, preferably by a piezoelectric element or other like device or element of the control unit.

Furthermore, processor 36 may determine 418 that an open circuit configuration, as in the open configuration of sensor circuit 117, corresponding to an absence or movement of the patient, exists for a period of time. If the open circuit configuration of system 110 exceeds a predetermined or programmed threshold delay period, the processor 36 will cause an output signal, such as an alarm signal, to be transmitted 420 to a nurse call circuit, receiver or receivers, monitoring equipment, or the like, and in some embodiments, an audible alarm signal will be generated by a provided piezoelectric element or other such device or element.

After an alarm signal has been transmitted, and in some embodiments audibly transmitted, the health care provider may place the system 110 in a hold or sleep mode 422 through input connections, and in some embodiments through one or more programming connections 61–65, or by external signals provided via conductor 32. The hold or sleep mode allows the health care provider to position the moved patient in the proper position relative to the patient sensing and monitoring system 110 or otherwise treat the patient without concurrent sensing, monitoring, and alarm functions reoccurring through control circuit 130. After relocation or treatment of the patient by the health care provider, the control unit 36 is then reset either automatically or manually to renew sensing, monitoring and alarm functions 424. Alternatively, the control circuit 130 may be programmed to determine that the time of absence determined in step 418 exceeds a threshold value, thus necessitating a sleep mode of control circuit 130 to reduce power consumption, such sleep mode, in some embodiments, initiating the powering down or shut off of the system 110.

Powering down the system may be accomplished through an off function of the system 110, such as a signal provided through input connections, and in some embodiments through one or a plurality of programming connections 61–65, or by external signals provided via conductor 32, to reduce power consumption of the internal power supply, such as battery 37, or that of an external power supply.

Numerous modifications and combinations of the embodiments disclosed will readily occur to those skilled in the art that are encompassed by this invention, and it is not desired to limit the invention to the exact construction and process shown and described above. For example, the present invention would encompass a configuration having other circuit topographies, potentially including other circuit components or combinations of circuit components, including analog or digital circuitry, to accomplish the various functionality and features of the present invention.

Furthermore, embodiments may vary from the process shown and described with regard to FIGS. 14*a* and 14*b* may provide the various processes and elements thereof in various combinations and sequences, such combinations and sequences encompassed by the disclosure of the present invention.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

The embodiments of the invention in which an exclusive property or privilege is claimed are defined as follows:

1. A patient sensing and monitoring system, comprising:
    a sensor for detecting the presence or absence of a patient;
    a control unit responsive to the sensor and operable to send a signal to a receiving device upon detecting the absence of the patient; and
    a container at least substantially encompassing the sensor and the control unit, wherein the container, sensor, and control unit configuration is conformable to a surface of a patient support apparatus, and wherein the control unit comprises one or more operation modes selected from the group consisting of a hold mode, and a sleep mode.

2. The system as described in claim 1 wherein said container comprises a sleeve.

3. The system as described in claim 1 wherein said system comprises a wheelchair covering.

4. The system as described in claim 1 wherein said system comprises a wheelchair pad.

5. The system as described in claim 1 wherein said system comprises a mattress covering.

6. The system as described in claim 1 wherein said system comprises a mattress pad.

7. The system as described in claim 1 wherein said system is configured as a component of a mattress.

8. The system as described in claim 1 wherein said system comprises a chair covering.

9. The system as described in claim 1 wherein said system comprises a chair pad.

10. The system as described in claim 1, wherein the one or more operation modes is controlled by a switch.

11. The system as described in claim 1 wherein said control unit is programmable.

12. The system as described in claim 11 wherein said control unit comprises a processor.

13. The system as described in claim 12 wherein said control unit is configured to process instructions and data.

14. The system as described in claim 13 wherein said control unit comprises at least one storage medium and wherein said instructions and data are stored on said at least one storage medium.

15. The system as described in claim 12 wherein said control unit comprises a piezoelectric element responsive to said processor and capable of providing an audible alarm.

16. The system as described in claim 1 wherein said control unit comprises a battery.

17. The system as described in claim 1 wherein said patient sensing and monitoring system is configured for external power supply.

18. The system as described in claim 1 wherein said control unit and said sensor are configured on a conformable substrate.

19. The system as described in claim 18 further comprising at least one flex element.

20. The system as described in claim 19 wherein said at least one flex element comprises at least one opening in said conformable substrate.

21. The system as described in claim 1 further comprising a wireless transmitter responsive to said control unit.

22. The system as described in claim 21 wherein said wireless transmitter is configured within said container and wherein said container at least substantially encompasses said wireless transmitter.

23. The system as described in claim 21 wherein said wireless transmitter comprises a radio frequency transmitter.

24. The system as described in claim 23 wherein said radio frequency transmitter is capable of transmission at about a frequency range of 900 MHz.

25. The system as described in claim 21 further comprising at least one wireless receiver responsive to said wireless transmitter.

26. The system as described in claim 25 wherein said wireless receiver is connected to patient monitoring equipment.

27. The system as described in claim 26 wherein said patient monitoring equipment comprises a nurse call circuit.

28. The system as described in claim 1 further comprising at least one output conductor connected to said control unit.

29. The system as described in claim 28 wherein said at least one output conductor comprises an electrical conductor selected from the group consisting of a cable, wire, lead, or plug conductor.

30. A patient sensing and monitoring system, comprising:
    a sensor for detecting the presence or absence of a patient, the sensor comprising an on-off switch circuit comprising a plurality of electrical connections;
    a control unit responsive to the sensor and operable to send a signal to a receiving device upon detecting the absence of the patient; and
    a container at least substantially encompassing the sensor and the control unit, wherein the container, sensor, and control unit configuration is conformable to a surface of a patient support apparatus.

31. The system as described in claim 30 wherein said on-off switch circuit comprises a first portion and a second portion, wherein said first and second portions are configured to responsively provide either an open switch configuration or a closed switch configuration responsive to the weight of a patient upon said sensor.

32. The system as described in claim 31 further comprising at least one support element adjacent said first and said second portions.

33. The system as described in claim 32 wherein said at least one support element comprises a spacer.

34. The system as described in claim 31 wherein said first portion comprises a first set of electrical connections and said second portion comprises a second set of electrical connections, and wherein said closed switch configuration comprises an electrical connection between at least one of said electrical connections of said first set and at least one of said electrical connections of said second set.

35. The system as described in claim 31 wherein said first portion comprises a top portion of said on-off switch circuit and said second portion comprises a bottom portion of said on-off switch circuit, and wherein either the top portion or the bottom portion is substantially adjacent a patient.

36. The system as described in claim 30 wherein said plurality of electrical connections comprise a network of electrical connections.

37. The system as described in claim 36 wherein said network of electrical connections comprises at least a portion of a series of substantially parallel network of electrical connections.

38. The system as described in claim 30 wherein said on-off switch circuit is conformable to the surface of the patient support apparatus.

39. The system as described in claim 38 wherein said on-off switch circuit is configured on a conformable substrate.

40. The system as described in claim 39 wherein said on-off switch circuit comprises a formed configuration on said conformable substrate, said formed configuration selected from the group consisting of an inked, etched, or deposited configuration.

41. The system as described in claim 39 further comprising at least one flex element.

42. The system as described in claim 41 wherein said at least one flex element comprises at least one opening in said conformable substrate.

43. A patient sensing and monitoring system, comprising:
a sensor for detecting the presence or absence of a patient;
a control unit responsive to the sensor and operable to send a signal to a receiving device upon detecting the absence of the patient, the control unit comprising a signal conditioner configured to filter static or transient signals generated by the sensor; and
a container at least substantially encompassing the sensor and the control unit, wherein the container, sensor, and control unit configuration is conformable to a surface of a patient support apparatus.

44. The system as described in claim 43 wherein said control unit comprises a processor and wherein said signal conditioner is configured to forward the filtered sensor signals to said processor.

45. The system as described in claim 44 wherein said signal conditioner is configured to provide said filtered sensor signals to said processor upon an open circuit configuration or closed circuit configuration.

46. The system as described in claim 45 wherein said open circuit configuration comprises an open switch configuration of said sensor and said closed circuit configuration comprises a closed switch configuration of said sensor.

47. A patient sensing and monitoring system, comprising:
a sensor for detecting the presence or absence of a patient;
a control unit responsive to the sensor and operable to send a signal to a receiving device upon detecting the absence of the patient, said control unit comprising a processor and at least one input connection, said at least one input connection providing programmable input to at least one storage medium and the processor as instructions; and
a container at least substantially encompassing the sensor and the control unit, wherein the container, sensor, and control unit configuration is conformable to a surface of a patient support apparatus.

48. The system as described in claim 47 wherein said at least one input connection comprises a plurality of programming connections.

49. A patient sensing and monitoring system, comprising:
a sensor for detecting the presence or absence of a patient;
a control unit responsive to the sensor and operable to send a signal to a receiving device upon detecting the absence of the patient, said control unit and said sensor being provided as a formed configuration on a conformable substrate, wherein said formed configuration is selected from the group consisting of an inked, etched, or deposited configuration; and
a container at least substantially encompassing the sensor and the control unit, wherein the container, sensor, and control unit configuration is conformable to a surface of a patient support apparatus.

50. A method of operationally unobtrusively sensing and monitoring a patient, comprising the steps of:
providing a sensor at least substantially encompassed by a container;
providing a control unit responsive to said sensor and at least substantially encompassed by said container;
conformably positioning said encompassed sensor and control unit on a patient support surface of a support apparatus;
monitoring for the presence, absence, or movement of a patient;
detecting an open circuit configuration of said sensor and control unit corresponding to the absence of the patient;
measuring an amount of time corresponding to said open circuit configuration and said absence of said patient;
determining if said amount of time exceeds a threshold delay period;
transmitting an alarm signal corresponding to the absence of the patient upon said step of determining if said amount of time exceeds a threshold delay period;
detecting a closed circuit configuration of the sensor and control unit corresponding to the presence of the patient; and
transmitting patient movement information responsive to said step of detecting a closed circuit configuration.

51. A method of sensing and monitoring a patient as described in claim 50 wherein said step of conformably positioning comprises conformably positioning said encompassed sensor and control unit on a patient support surface of a support apparatus selected from the group consisting of a bed, a mattress, a chair, or a wheelchair.

52. A method of sensing and monitoring a patient as described in claim 50 further comprising the steps of:
powering said control unit and said sensor; and
connecting said control unit to external patient monitor equipment.

53. A method of sensing and monitoring a patient as described in claim 52 wherein said step of connecting said control unit to external patient monitoring equipment comprises connecting said control unit to a nurse call circuit.

54. A method of sensing and monitoring a patient as described in claim 52 wherein said step of connecting said control unit comprises providing wireless connection.

55. A method of sensing and monitoring a patient as described in claim 54 wherein said step of providing wireless connection comprises providing a wireless transmitter connected to said control unit, wherein said wireless transmitter is capable of transmitting signals to at least one receiver external of said wireless transmitter, said control unit, and said sensor.

56. A method of sensing and monitoring a patient as described in claim 52 wherein said step of powering said control unit and sensor comprises activating an on function of said control unit.

57. A method of sensing and monitoring a patient as described in claim 56 wherein said step of powering said control unit and sensor comprises providing an external power supply.

58. A method of sensing and monitoring a patient as described in claim 56 wherein said step of powering said control unit and sensor comprises providing power from a battery connected to said control unit and sensor.

59. A method of sensing and monitoring a patient as described in claim 50 wherein said control unit is programmable, and further comprising the step of:

programming said control unit with instructions and data.

60. A method of sensing and monitoring a patient as described in claim 59 wherein said step of programming comprises programming instructions and data selected from the group consisting of timer data, clock data, hold instructions, or sleep instructions.

61. A method of sensing and monitoring a patient as described in claim 59 wherein said step of programming comprises storing said instructions and data on storage media.

62. A method of sensing and monitoring a patient as described in claim 59 wherein said step of programming comprises entering said instructions and data through at least one input connection.

63. A method of sensing and monitoring a patient as described in claim 59 wherein said step of programming comprises providing instructions and data to said control unit, said instructions selected from instructions of the group consisting of software, program code, or firmware.

64. A method of sensing and monitoring a patient as described in claim 50 wherein said step of monitoring comprises activating a monitoring mode of said control unit and said sensor.

65. A method of sensing and monitoring a patient as described in claim 64 wherein said of activating comprises generating a signal through closed circuit configuration of said control unit and said sensor.

66. A method of sensing and monitoring a patient as described in claim 65 wherein said step of generating a signal comprises creating a closed switch configuration of said sensor.

67. A method of sensing and monitoring a patient as described in claim 66 wherein said step of creating a closed switch configuration of said sensor comprises positioning the patient on said sensor.

68. A method of sensing and monitoring a patient as described in claim 50 wherein said step of detecting an open circuit configuration of said sensor and control unit corresponding to the absence of the patient comprises detecting an open switch configuration of said sensor.

69. A method of sensing and monitoring a patient as described in claim 68 wherein said step of detecting an open switch configuration comprises detecting the removal of patient pressure from said sensor.

70. A method of sensing and monitoring a patient as described in claim 50 wherein said step of detecting an open circuit configuration of said sensor and control unit corresponding to the absence of the patient comprises detecting a time intervals.

71. A method of sensing and monitoring a patient as described in claim 50 further comprising the step of transmitting an alarm signal responsive to said step of detecting an open circuit configuration of said sensor and control unit corresponding to the absence of the patient.

72. A method of sensing and monitoring a patient as described in claim 71 further comprising the steps of:

initiating a hold or sleep mode of said control unit and sensor;

positioning a patient on said sensor;

rescuing the control unit and sensor; and monitoring for the presence, absence, or movement of the patient on the patient support surface of the support apparatus.

73. A method of sensing and monitoring a patient as described in claim 72 wherein said step of initiating a hold or sleep mode comprises activating a signaling device of said control unit.

74. A method sensing and monitoring a patient as described in claim 73 wherein said step of activating a signaling device of said control unit comprises operating a switch.

75. A method of sensing and monitoring a patient as described in claim 50 further comprising the step of monitoring the energy level of a battery of said control unit.

76. A method of sensing and monitoring a patient as described in claim 75 further comprising the step of transmitting an alarm signal responsive to a low energy level of said battery to monitoring equipment external to said control unit and said sensor.

77. A method of sensing and monitoring a patient as described in claim 76 further comprising the step of generating an audible alarm signal responsive to said low energy level.

78. A method of sensing and monitoring a patient as described in claim 50 wherein said step of detecting a closed circuit configuration of said sensor and control unit corresponding to the presence of the patient comprises detecting a closed switch configuration of said sensor.

79. A method of sensing and monitoring a patient as described in claim 78 wherein said step of detecting a closed switch configuration of said sensor comprises detecting a closed switch configuration of said sensor corresponding to movement of the patient.

80. A method of sensing and monitoring a patient as described in claim 78 wherein said step of detecting a closed switch configuration comprises detecting the weight of a patient on said sensor corresponding to movement or non-movement of the patient.

81. A method of sensing and monitoring a patient as described in claim 80 wherein said step of detecting the weight of a patient comprises detecting a change in the weight of the patient on said sensor.

82. A method of sensing and monitoring a patient as described in claim 50 wherein said step of transmitting patient movement information comprises transmitting patient movement information to external patient monitoring equipment.

83. A method of sensing and monitoring a patient as described in claim 82 further comprising a step of transmitting an alarm signal to external patient monitoring equipment responsive to said patient movement information.

84. A method of sensing and monitoring a patient as described in claim 83 wherein said step of transmitting an alarm signal comprises transmitting a periodic alarm signal.

85. A method of sensing and monitoring a patient as described in claim 83 further comprising the step of transmitting an audible alarm responsive to said patient movement information.

86. A method of sensing and monitoring a patient as described in claim 50 further comprising the step of powering down the control unit and sensor.

* * * * *